(12) United States Patent
Parker

(10) Patent No.: US 10,518,107 B2
(45) Date of Patent: Dec. 31, 2019

(54) PHOTOSENSITIVE CARDIAC RHYTHM MODULATION SYSTEMS

(71) Applicant: President and Fellows of Harvard College, Cambridge, MA (US)

(72) Inventor: Kevin Kit Parker, Waltham, MA (US)

(73) Assignee: President and Fellows of Harvard College, Cambridge, MA (US)

(*) Notice: Subject to any disclaimer, the term of this patent is extended or adjusted under 35 U.S.C. 154(b) by 1238 days.

(21) Appl. No.: 14/261,693

(22) Filed: Apr. 25, 2014

(65) Prior Publication Data

US 2014/0236267 A1 Aug. 21, 2014

Related U.S. Application Data

(63) Continuation of application No. 13/808,411, filed as application No. PCT/US2011/043027 on Jul. 6, 2011, now abandoned.

(60) Provisional application No. 61/361,652, filed on Jul. 6, 2010, provisional application No. 61/367,075, filed on Jul. 23, 2010.

(51) Int. Cl.
*A61K 35/34* (2015.01)
*A61N 5/06* (2006.01)
*C12N 5/071* (2010.01)

(52) U.S. Cl.
CPC ............ *A61N 5/0622* (2013.01); *A61K 35/34* (2013.01); *C12N 5/069* (2013.01)

(58) Field of Classification Search
None
See application file for complete search history.

(56) References Cited

U.S. PATENT DOCUMENTS

| | | |
|---|---|---|
| 8,492,150 B2 | 7/2013 | Parker et al. |
| 8,748,181 B2 | 6/2014 | Kuo et al. |
| 8,999,378 B2 | 4/2015 | Parker et al. |
| 9,012,172 B2 | 4/2015 | Parker et al. |
| 9,068,168 B2 | 6/2015 | Feinberg et al. |
| 9,383,350 B2 | 7/2016 | Parker et al. |
| 2004/0009566 A1 | 1/2004 | Okano et al. |
| 2004/0078090 A1 | 4/2004 | Binette et al. |
| 2004/0101819 A1 | 5/2004 | Montemagno et al. |
| 2005/0080402 A1 | 4/2005 | Santamore et al. |
| 2005/0085847 A1 | 4/2005 | Galdonik et al. |
| 2006/0003439 A1 | 1/2006 | Ismagilov et al. |
| 2007/0060815 A1 | 3/2007 | Martin et al. |
| 2008/0085265 A1 | 4/2008 | Schneider et al. |
| 2009/0054954 A1 | 2/2009 | Foley et al. |
| 2010/0196432 A1 | 8/2010 | Feinberg et al. |
| 2011/0189719 A1 | 8/2011 | Kuo et al. |
| 2011/0250585 A1 | 10/2011 | Ingber et al. |
| 2012/0134570 A1 | 5/2012 | Trumbull et al. |
| 2012/0135448 A1 | 5/2012 | Parker et al. |
| 2012/0142556 A1 | 6/2012 | Parker et al. |
| 2013/0046134 A1 | 2/2013 | Parker et al. |
| 2013/0312638 A1 | 11/2013 | Parker et al. |
| 2013/0330378 A1 | 12/2013 | Parker et al. |
| 2014/0236267 A1* | 8/2014 | Parker .................... A61K 35/34 607/88 |
| 2014/0322515 A1 | 10/2014 | Parker et al. |
| 2015/0182679 A1 | 7/2015 | Parker et al. |
| 2015/0253307 A1 | 9/2015 | Parker et al. |
| 2015/0354094 A1 | 12/2015 | Parker et al. |
| 2016/0003806 A1 | 1/2016 | Parker et al. |
| 2017/0016875 A1 | 1/2017 | Parker et al. |

FOREIGN PATENT DOCUMENTS

| | | |
|---|---|---|
| WO | WO-2012/131360 A2 | 10/2012 |
| WO | WO-2013/086512 A2 | 6/2013 |
| WO | WO-2013/115896 A2 | 8/2013 |
| WO | WO-2016/007879 A1 | 1/2016 |
| WO | WO-2016/069142 A2 | 5/2016 |
| WO | WO-2016/191179 A1 | 12/2016 |
| WO | WO-2017/027390 A1 | 2/2017 |
| WO | WO-2017/087759 A1 | 5/2017 |
| WO | WO-2018/027105 A1 | 2/2018 |

OTHER PUBLICATIONS

International Search Report from PCT/US2011/043027 dated Jul. 6, 2011.
Alford et al., "Biohybrid thin films for measuring contractility in engineered cardiovascular muscle" *Biomaterials* 31, May 2010, 3613-3621.
Badrossamay, M.R. et al. "Nanofiber assembly by rotary jet-spinning." Nano Letters, May 2010;10(6):2257-2261.
Bray et al., "Sarcomere Alignment is Regulated by Myocyte Shape" *Cell Motility and the Cytoskeleton*, Aug. 2008, 65(8), pp. 641-651.
Bursac et al., "Cardiomyocyte cultures with controlled macroscopic anisotropy." *Circulation Rearch*, Dec. 2002, vol. 91, pp. e45-e54.
Grosberg et al., "Ensembles of engineered cardiac tissues for physiological and pharmacological study: Heart on a chip." Lab Chip, Nov. 2011, vol. 11, p. 4165.
Lehnert et al., "Cell behavior on micropatterned substrata: limits of extracellular matrix geometry for spreading and adhesion." *Journal of Cell Science*, Jan. 2004, vol. 117 (1), pp. 41-52.
Mao et al., "Capillary isoelectric focusing with whole column imaging detection for analysis of proteins and peptides," J. Biochem. Biophys. Methods, Feb. 1999, 39:93-110.
Park et al., "Real-Time Measurement of the Contractile Forces of Self-Organized Cardiomyocytes on Hybrid Biopolymer Microcantilevers," Anal. Chem. Oct. 2005, 77:6571-6580.
Parker et al., "Extracellular matrix, mechanotransduction and structural hierarchies in heart tissue engineering." Phil Trans R. Soc B, Epub, Jun. 22, 2007, vol. 362, pp. 1267-1279.
Spring, Kenneth R. "Electronic Imaging in Neuroscience," Curr. Protoc. Neurosci. May 2002, 2.4.1-2.4.9.

(Continued)

*Primary Examiner* — Michael D Burkhart
(74) *Attorney, Agent, or Firm* — McCarter & English, LLP; Maria Laccotripe Zacharakis; Deborah L. Nagle

(57) ABSTRACT

Photosensitive cardiac rhythm modulation structures and systems are described. A genetically-engineered tissue comprising a population of pacing cells expressing a photosensitive membrane transport mechanism that is responsive to light of a particular wavelength(s) combined with one or more of a light source, a power generator, and a sensor provides pacemaker and/or defibrillator function to a subject. The systems further provide in vitro model systems for electrophysiological studies.

23 Claims, 9 Drawing Sheets

(56) References Cited

OTHER PUBLICATIONS

Xi et al., "Development of a Self-Assembled Muscle-Powered Piezoelectric Microgenerator", NSTI-Nanotech, 2004, vol. 1, pp. 3-6. (The month of publication is not available; however, the year of publication is sufficiently earlier than the effective U.S. filing date and any foreign priority date so that the particular month of publication is not in issue.).
Yang et al., "Fabrication of well-defined PLGA scaffolds using novel microembossing and carbon dioxide bonding," Biomaterials, Sep. 2005, vol. 26, pp. 2585-2594.
U.S. Appl. No. 12/443,890, filed Apr. 8, 2010, US 2010/0196432, Abandoned.
U.S. Appl. No. 12/223,560 U.S. Pat. No. 8,492,150, filed Feb. 25, 2009, US 2009/0317852, Granted.
U.S. Appl. No. 13/922,432 U.S. Pat. No. 9,383,350, filed Jun. 20, 2013, US 2014/0004553, Granted.
U.S. Appl. No. 12/680,277 U.S. Pat. No. 9,068,168, filed Sep. 1, 2010, US 2010/0330644, Granted.
U.S. Appl. No. 12/994,187 U.S. Pat. No. 8,748,181, filed Mar. 17, 2011, US 2011/0189719, Granted.
U.S. Appl. No. 13/120,003 U.S. Pat. No. 8,999,378, filed Jun. 2, 2011, US 2012/0029416, Granted.
U.S. Appl. No. 13/878,383, filed Aug. 16, 2013, US 2013/0330378, Abandoned.
U.S. Appl. No. 13/318,227 U.S. Pat. No. 9,012,172, filed Feb. 21, 2012, US 2012/0142556, Granted.
U.S. Appl. No. 14/642,906, filed Mar. 10, 2015, US 2016/0003806, Allowed.
U.S. Appl. No. 13/580,191, filed Oct. 31, 2012, US 2013/0046134, Abandoned.
U.S. Appl. No. 13/808,411, filed Jan. 4, 2013, N/A, Abandoned.
U.S. Appl. No. 14/362,287, filed Jun. 2, 2014, US-2014-0342394, Allowed.
U.S. Appl. No. 14/415,945, filed Jan. 20, 2015, US 2015/0182679, Allowed.
U.S. Appl. No. 14/429,826, filed Mar. 20, 2015, US 2015/0253307, Published.
U.S. Appl. No. 15/116,258, filed Aug. 3, 2016, N/A, Pending.
PCT/US2015/039983, filed Jul. 10, 2015, WO 2016/007879, Published.
PCT/US2015/051818, filed Sep. 24, 2015, WO 2016/069142, Published.
PCT/US2016/033168, filed May 19, 2016, WO 2016/191179, Published.
PCT/US2016/045813, filed Aug. 5, 2016, WO 2017/027390, Published.
International Search Report and Written Opinion from PCT/US2015/016395, dated Jan. 6, 2016.

* cited by examiner

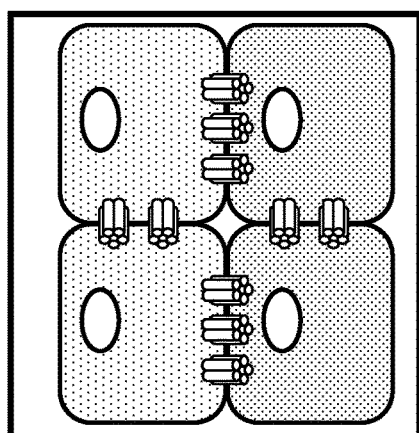
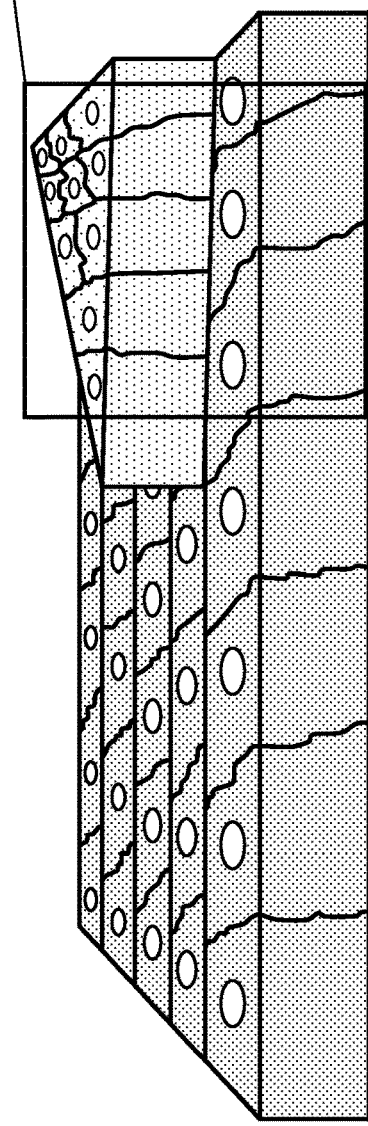
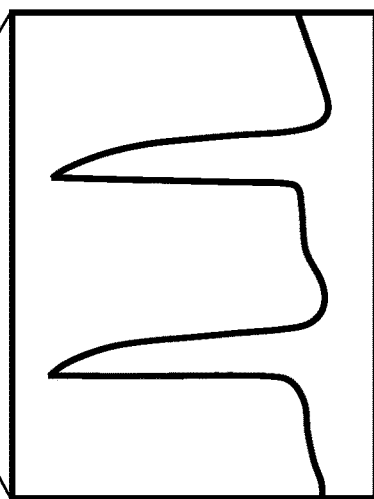
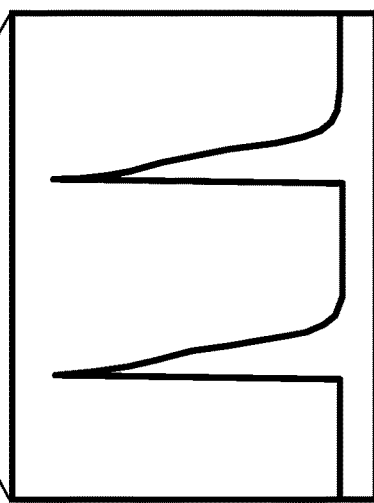
Fig. 5B
Cardiomyocytes
Pacemaking Cells
PDMS Layer
Fig. 5A
Fig. 5D
Fig. 5C

PHOTOSENSITIVE CARDIAC RHYTHM MODULATION SYSTEMS

RELATED APPLICATIONS

This application is a continuation application of U.S. patent application Ser. No. 13/808,411, filed on Jan. 4, 2013, which is a 35 U.S.C. § 371 National Stage filing of International Application No. PCT/US2011/043027, filed on Jul. 6, 2011, which claims the benefit of and priority to U.S. Provisional Patent Application Ser. No. 61/361,652, filed on Jul. 6, 2010, and U.S. Provisional Patent Application Ser. No. 61/367,075, filed on Jul. 23, 2010. The entire contents of each of the foregoing incorporated herein by reference.

GOVERNMENT SUPPORT

This invention was made with award HL079126 from the National Institutes of Health. The United States Government has certain rights in the invention.

BACKGROUND OF THE INVENTION

Pacemaker and defibrillator devices use electrical impulses to regulate beating of the heart. Current implantable artificial pacemakers and defibrillators rely on a programmable electronic device and wired electrodes to electrically stimulate and synchronize beating of the myocardium (pacemaker) or to correct cardiac arrhythmia (defibrillator). However, these implantable devices are unresponsive to autonomic heart rate modulation, require invasive surgical implantation and replacement every 5-10 years, are susceptible to temporary malfunction in the presence of magnets, e.g., metal detectors or MRI machines, or environmental noise, and increase the patient's inflammatory response and risk of infection. They have a limited battery life and their long-term use has been associated with permanent cardiac tissue damage. In addition, these electronic devices are often unsuitable for pediatric patients (see, e.g., emedicine.medscape.com/article/780825-overview).

Furthermore, implantable electrical cardiac defibrillators function by delivering a large, brief electric shock to reset a tachycardic/fibrillating heart and restore normal beating. Like pacemakers, the defibrillators must be implanted surgically and are prone to mechanical failure. A major complaint of patients with implanted defibrillators is the extreme pain from the electric shock produced by the devices.

Biological pacemakers are one alternative to artificial electrical pacing therapy. Biological pacemakers are responsive to autonomic modulation, require no external power source or replacement, present minimal inflammatory response, can be permanent, and can be autologous. Attempts at restoring cardiac automaticity with biologics have recently focused on two main approaches: gene therapy and cell transplantation (reviewed in M R Rosen et al., *Anat. Rec. Part A* 280A: 1046-1052, 2004). Gene therapy approaches introduce genes, such as the pacemaker gene, HCN2, directly into myocardial cells to restore or enhance automaticity. For example, adenovirus carrying an HCN2 construct has been injected into the left ventricular bundle branch system of canine hearts. Upon vagal stimulation, transgenic hearts demonstrated a more rapid heart rate than control hearts. Cell transplantation approaches involve transplanting isolated spontaneously active or genetically-engineered cells directly into the myocardium. For example, adult mesenchymal stem cells have been transformed with HCN2. The transformed stem cells were injected into the left ventricular anterior wall of a canine heart and were capable of stimulating heart rhythms (M R Rosen et al., *Anat. Rec. Part A* 280A: 1046-1052, 2004).

These short-term studies demonstrate the potential of biological pacemakers. Biological defibrillators have not, as yet, been explored. However, for both technologies, miniaturized systems and a minimally invasive means to access and regulate the cellular devices would facilitate and optimize control and repair of cardiac function in patients. Thus, there is a need in the art for biological pacemakers and/or defibrillators which are less invasive and more effective in regulating beating of the heart.

SUMMARY OF THE INVENTION

The present invention provides a biologically engineered tissue comprising a population of pacing, e.g., cardiac cells, e.g., pacemaker cells, expressing a photosensitive membrane transport mechanism, such as a light-gated ion channel or a light-driven ion pump. The photosensitive membrane transport mechanism may advantageously be responsive to photostimulation, e.g., responsive to light of a particular wavelength(s). Thus, photostimulation of the membrane transport mechanism may advantageously affect membrane potential of the pacing cells, e.g., cardiac cells, e.g., pacemaker cells. For example, the pacing cells may be selectively and controllably depolarized or hyperpolarized in response to photostimulation.

In one aspect of the invention, genetically engineered photosensitive tissues are provided. The genetically engineered photosensitive tissues include a population of pacing cells expressing a photosensitive membrane transport mechanism. The photosensitive membrane transport mechanism may include a light-gated ion channel and/or a light-driven ion pump. In one embodiment, the photosensitive membrane transport mechanism comprises a rhodopsin. In one embodiment the rhodopsin is selected from the group consisting of channelrhodopsin-1, channelrhodopsin-2, V-channelrhodopsin-1, halorhodopsin, and combinations thereof.

In another aspect, the present invention provides methods of preparing genetically engineered photosensitive tissues. The methods include transfecting a population of cells selected from the group consisting of sinoatrial node cardiac cells, atrioventricular cardiac cells, cardiac conduction cells, cardiac progenitor cells, embryonic stem cells, induced pluripotent stem cells, adult mesenchymal stem cells, adult cardiac resident stem cells, and other adult stem cells, with a nucleic acid molecule encoding a photosensitive membrane transport mechanism. The photosensitive membrane transport mechanism may include a light-gated ion channel and/or a light-driven ion pump. In one embodiment, the photosensitive membrane transport mechanism comprises a rhodopsin. In one embodiment, the rhodopsin is selected from the group consisting of channelrhodopsin-1, channelrhodopsin-2, V-channelrhodopsin1, halorhodopsin, and combinations thereof.

In yet another aspect, the present invention also provides photosensitive cardiac rhythm modulation tissue structures. The photosensitive cardiac rhythm modulation tissue structures include a flexible polymer layer and a genetically engineered photosensitive tissue which is attached to the flexible polymer layer.

In one aspect, the present invention further provides photosensitive cardiac rhythm modulation systems. The photosensitive cardiac rhythm modulation systems include a photosensitive cardiac rhythm modulation tissue structure, a light source adapted to provide photostimulation to the photosensitive cardiac rhythm modulation tissue structure, and a sensor array. The photosensitive cardiac rhythm modulation systems may further comprise a power generator. In one embodiment, the light source is selected from the group consisting of a light emitting diode and a diode laser, and wherein the light source is coupled to an optical fiber.

In one embodiment, the genetically engineered photosensitive tissue of a photosensitive cardiac pacemaker comprising a photosensitive cardiac rhythm modulation system is capable of depolarizing, generating an action potential, and beating in response to photostimulation. In another embodiment, the genetically engineered photosensitive tissue of a photosensitive cardiac defibrillator comprising a photosensitive cardiac rhythm modulation system is capable of hyperpolarizing, suppressing generation of an action potential, and suppressing beating in response to photostimulation.

In another aspect, the present invention provides methods of treating cardiac dysfunction in a subject in need thereof. The methods include attaching a photosensitive cardiac rhythm modulation system in the vicinity of cardiac tissue of the subject. The photosensitive cardiac rhythm modulation systems may be capable of stimulating an action potential in response to photostimulation, capable of suppressing an action potential in response to photostimulation, or capable of both stimulating and suppressing an action potential in response to activation by light, wherein the wavelength of the light determines whether the action potential is stimulated or suppressed.

In yet another aspect, the present invention provides methods of treating cardiac dysfunction in a subject in need thereof. The methods include the steps of contacting a photosensitive cardiac rhythm modulation tissue structure to cardiac tissue of the subject, allowing the genetically engineered photosensitive tissue to become electrically coupled with the cardiac tissue of the subject, and photostimulating the genetically engineered photosensitive tissue, thereby treating cardiac dysfunction in the subject.

In yet another aspect, the present invention provides methods of treating cardiac dysfunction in a subject in need thereof. The methods include contacting a pacing cell of the subject with a nucleic acid molecule comprising a photosensitive membrane transport mechanism, and photostimulating the genetically engineered photosensitive tissue, thereby treating cardiac dysfunction in the subject.

In one aspect, the present invention provides an in vitro model for electrophysiological studies of cardiac function. The in vitro model includes one or more photosensitive cardiac rhythm modulation tissue structures.

In another aspect, the present invention provides methods for identifying a compound that modulates a cardiac tissue activity. The methods include the steps of providing an in vitro model for electrophysiological studies of cardiac function, contacting the model with a test compound, and evaluating the activity of the model in response to the test compound, thereby identifying a compound that modulates a cardiac tissue activity.

The present invention is further described by the following detailed description and drawings.

BRIEF DESCRIPTION OF THE DRAWINGS

FIG. 3 depicts in vitro testing of a pacing MTF.

FIGS. 5A-5D depict in vitro studies, in which an engineered anisotropic tissue is cultured on a PDMS covered glass cover slip with a pacing MTF (wedge). FIG. 5A depicts anisotropic tissue (dark grey); Pacing MTF (wedge of cells over anisotropic tissue); Cell nuclei (light gray). FIG. 5B depicts an enlargement of the area in square in FIG. 5A. Upper cells are MTF and lower cells are anisotropic tissue. Gap junctions spontaneously form, electrically coupling the pacing MTF to the ventricular tissue. FIG. 5C depicts optical action potentials which are recorded from an area of engineered anisotropic tissue and display typical sharp upstrokes. FIG. 5D depicts optical action potentials recorded from an area of engineered anisotropic tissue in direct contact with a pacing MTF display slow diastolic depolarization due to the pacing current supplied by the MTF.

FIG. 6 depicts two embodiments of an optical pacemaker.

DETAILED DESCRIPTION OF THE INVENTION

The present invention provides a biologically engineered tissue comprising a population of pacing, e.g., cardiac, e.g., pacemaker cells, expressing a photosensitive membrane transport mechanism, such as a light-gated ion channel or a light-driven ion pump. The photosensitive membrane transport mechanism may advantageously be responsive to photostimulation, e.g., responsive to light of a particular wavelength(s). Thus, photostimulation of the membrane transport mechanism may advantageously affect membrane potential of the pacing cells, e.g., pacemaker cells, e.g., the cardiac cells may be selectively and controllably depolarized or hyperpolarized in response to photostimulation.

Figure 1:
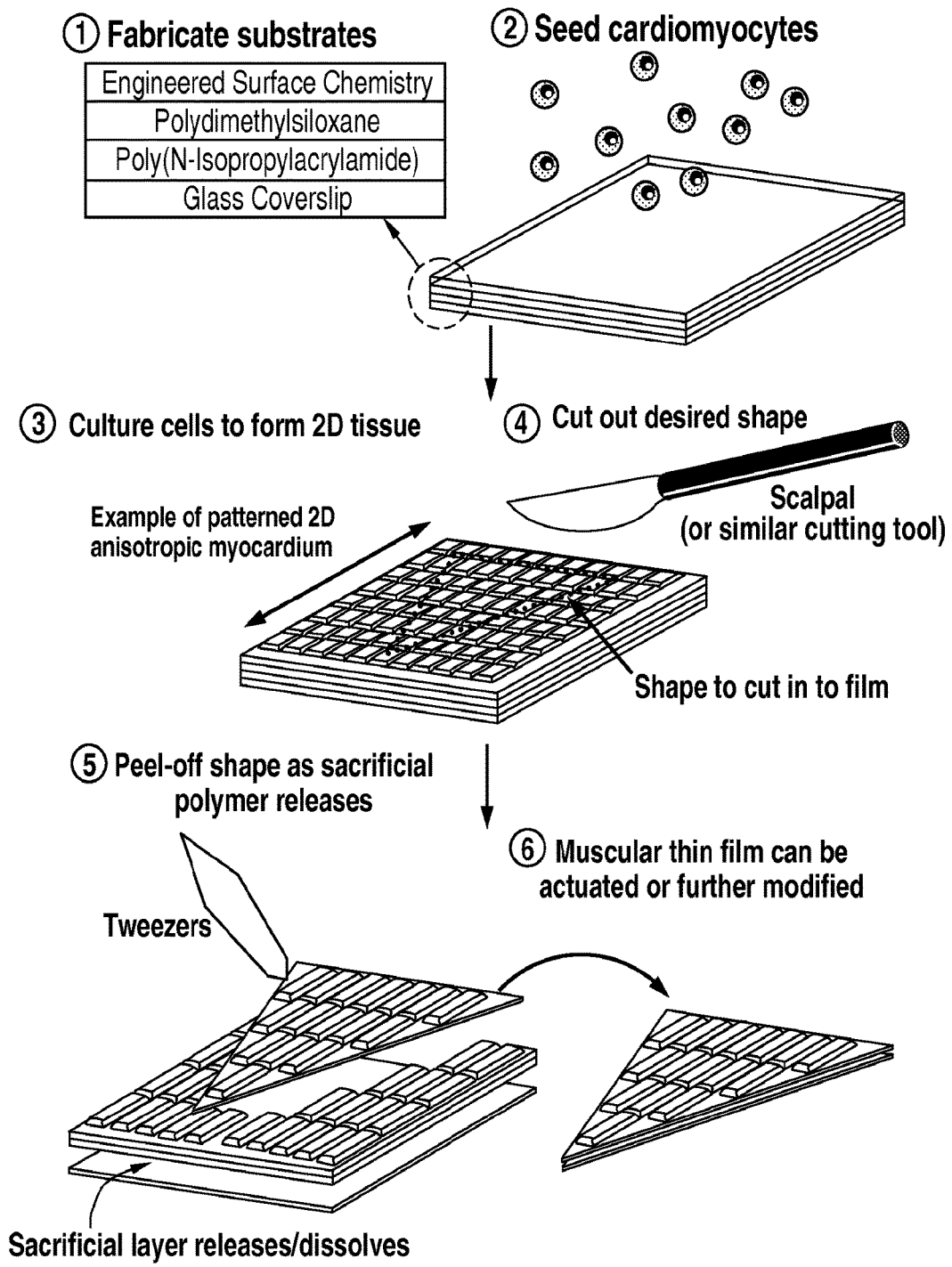
FIG. 1 is a schematic depicting one embodiment for the fabrication of a Muscle Thin Film (MTF). (1) The substrates are fabricated on a glass cover slip spin coated with PIPAAM that provides temporary adhesion to a PDMS top layer. The PDMS is patterned with ECM, fibronectin (FN) in this case, to elicit cell adhesion and growth. (2) Substrates are placed in culture with a cell suspension to allow pacemaking cells to settle and adhere to the surface. (3) MTFs are cultured in an incubator until the pacemaking cells form a two-dimensional tissue. (4) A desired shape is cut in the tissue/PDMS film. (5) The PIPAAM is dissolved by lowering the bath temperature below 35° C., releasing the MTF. The cutout shape floats free or is gently peeled off. (6) The free-standing MTF is then used directly or modified further by folding into a three-dimensional conformation.
Figure 2:
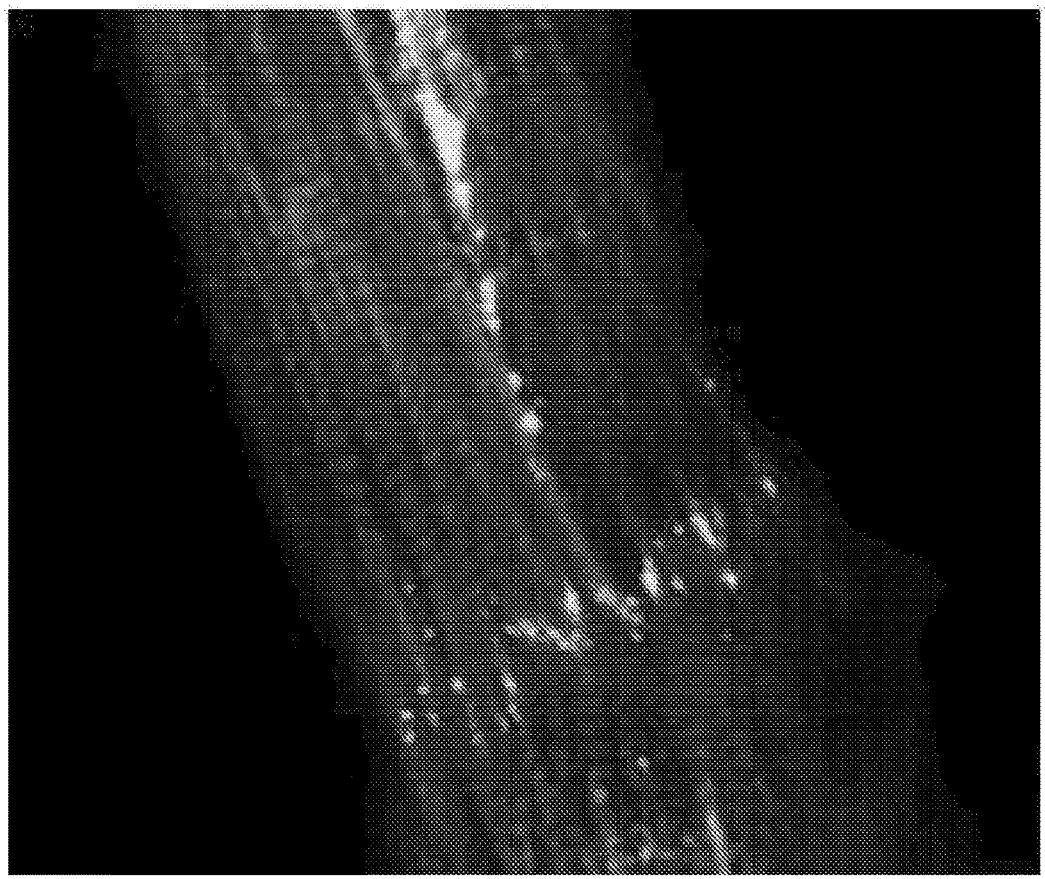
FIG. 2 depicts spontaneous gap junction formation between cardiac myocytes cultured on a micropatterned substrate. Connexin 43 (white), sarcomere Z-lines are indicated by fluorescent staining of α-actinin (gray).
Figure 3A:
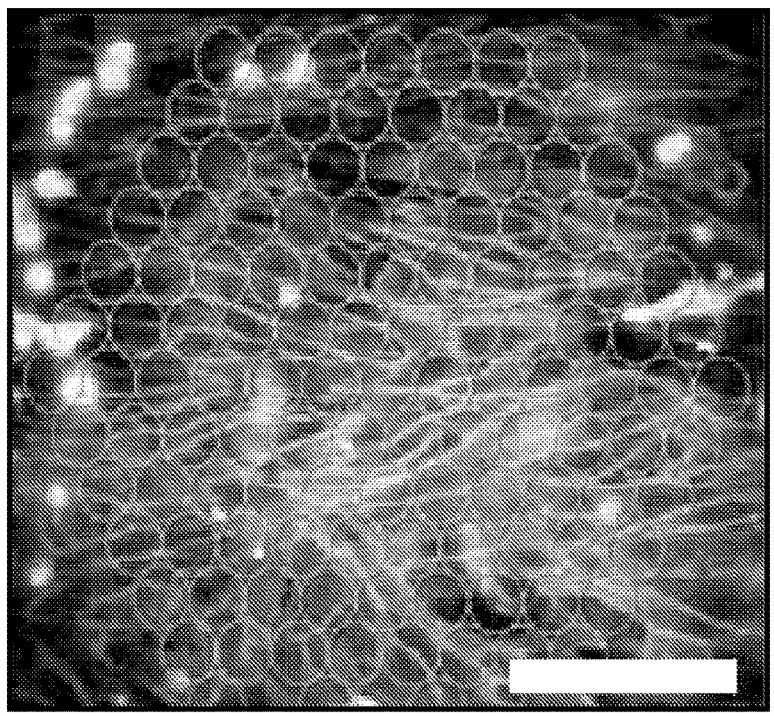
FIG. 3A depicts an engineered myocardium on a 128 channel optical mapping system. The optical fiber array is depicted with a white circular outline for each photodiode. The cells are stained with RH237, a potential-sensitive dye. Scale bar is 100 μm.
Figure 3B:
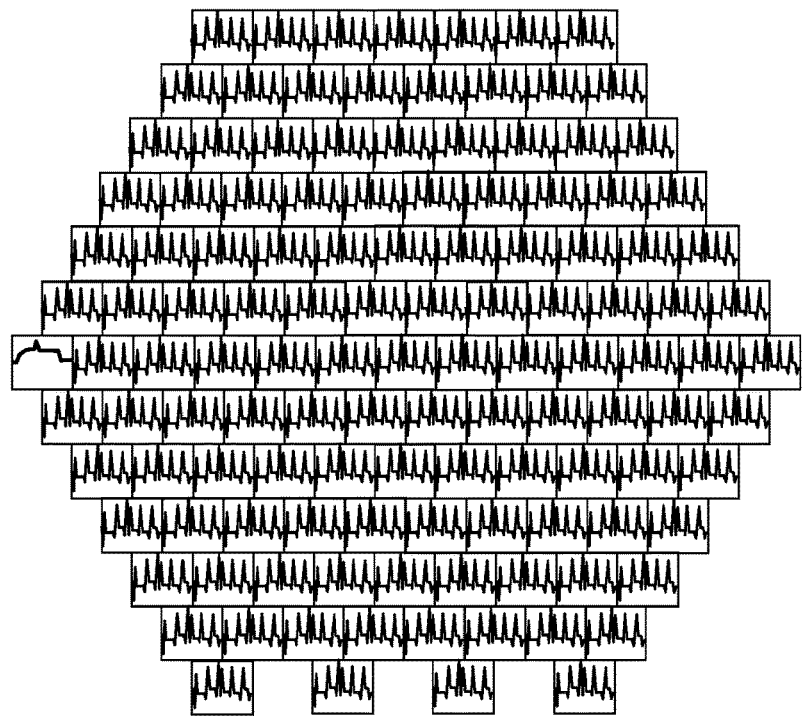
FIG. 3B depicts action potential traces recorded for each photodiode.
Figure 3C:
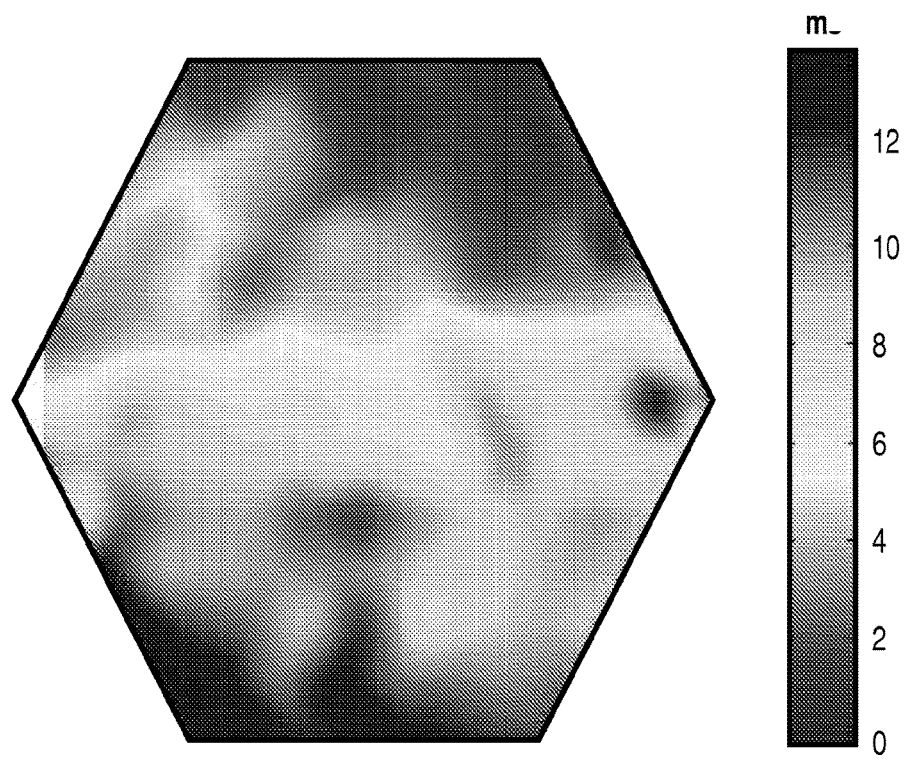
FIG. 3C depicts an activation map illustrating the arrival time of the action potential at points in the tissue.
Figure 3D:
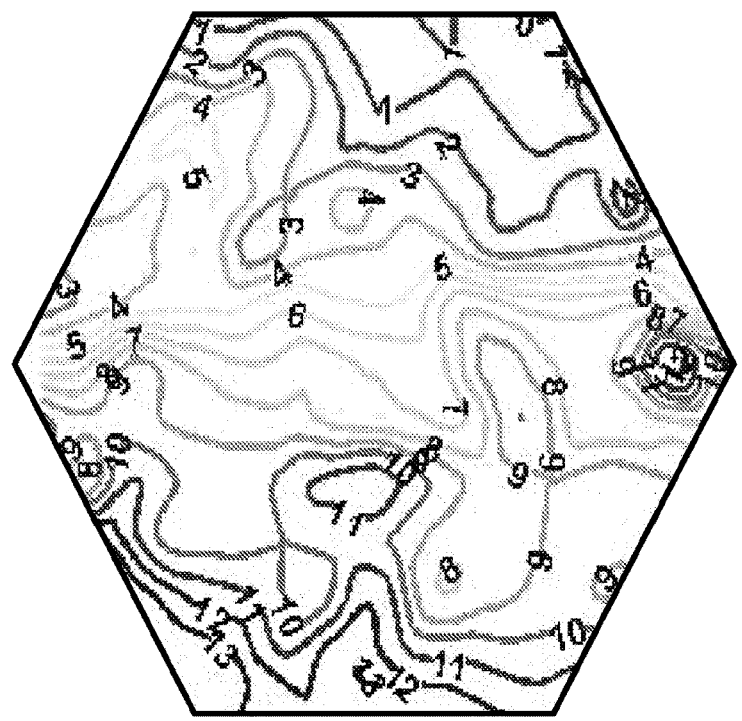
FIG. 3D depicts isochrones mapping to the activation map are used to precisely calculate the action potential conduction velocity as it propagates through the tissue.
Figure 3E:
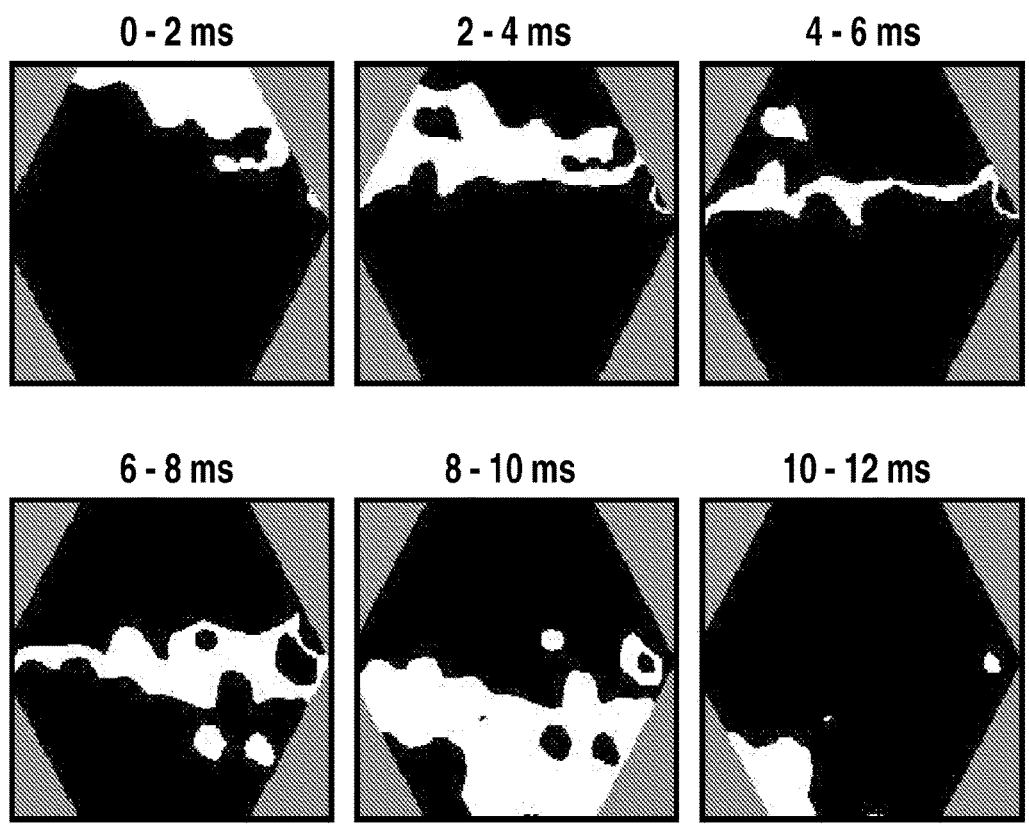
FIG. 3E depicts time sequences showing when the action potential arrives at different parts of the tissue. In these experiments, the tissue was paced by bipolar point stimulation. When a pacing MTF is fixed onto the tissue, these activation maps are used to determine if the pacing MTF is electrically controlling the whole tissue construct. Calculations of the conduction velocity from the arrival times in the isochrones are used to verify gap-junction coupling between the pacing MTF and the myocardium. Local conduction velocity can be calculated from conduction velocity vector fields according to the method of Bayly et al. (*IEEE Trans Biomed Eng*, 45: 563-71, 1998).

The present invention is based, at least in part, on the development of anisotropic muscle thin films (MTFs) that function as photosensitive cardiac rhythm modulation tissue structures and systems, e.g., pacemakers and/or defibrillators, in response to photostimulation. One method for preparing an MTF for use in the present invention is shown schematically in FIG. 1 and described in Example 1. The anisotropic MTFs are fabricated on a biocompatible polymer patterned with extracellular matrix (ECM) substrates, e.g., fibronectin, laminin, collagens. The polymer/ECM scaffolds are incubated with a suspension of cells, e.g., pacing cells, e.g., pacemaking cells, which express a photosensitive membrane transport mechanism and which adhere to the surface and form a 2-dimensional tissue of nodal, pacemaking myocardium. The micropatterning of ECM substrates on the biocompatible polymer allows the cells to adhere to the polymer/ECM scaffold in an anisotropic arrangement that mimics the organization of myocardium in vivo. The cells comprising anisotropic MTFs are electrically coupled via gap junctions, as shown in FIG. 2, and are capable of transducing an action potential in vitro. When transplanted in vivo, anisotropic, pacing MTFs successfully pace native heart tissue and/or allow conduction between cell populations, thus functioning as a pacemaker. The same methods using appropriate cell types may be used to fabricate a biological defibrillator.

The cardiac rhythm modulation tissue structure has cells oriented via engineered surface chemistries to produce an anisotropic pacemaking tissue. FIG. 3 shows propagation of an action potential across a cardiac rhythm modulation structure. It is advantageous to make the cells of the cardiac rhythm modulation structure anisotropic with the cardiac cells aligned vertically from the superior vena cava (SVC) to inferior vena cava (IVC). This cellular arrangement insulates the cardiac rhythm modulation structure from the surrounding atrial myocytes by taking advantage of the native "block zone" (Bleeker et al., *Circ Res* 46: 11-22, 1980) and improving the safety of conduction.

Figure 4:
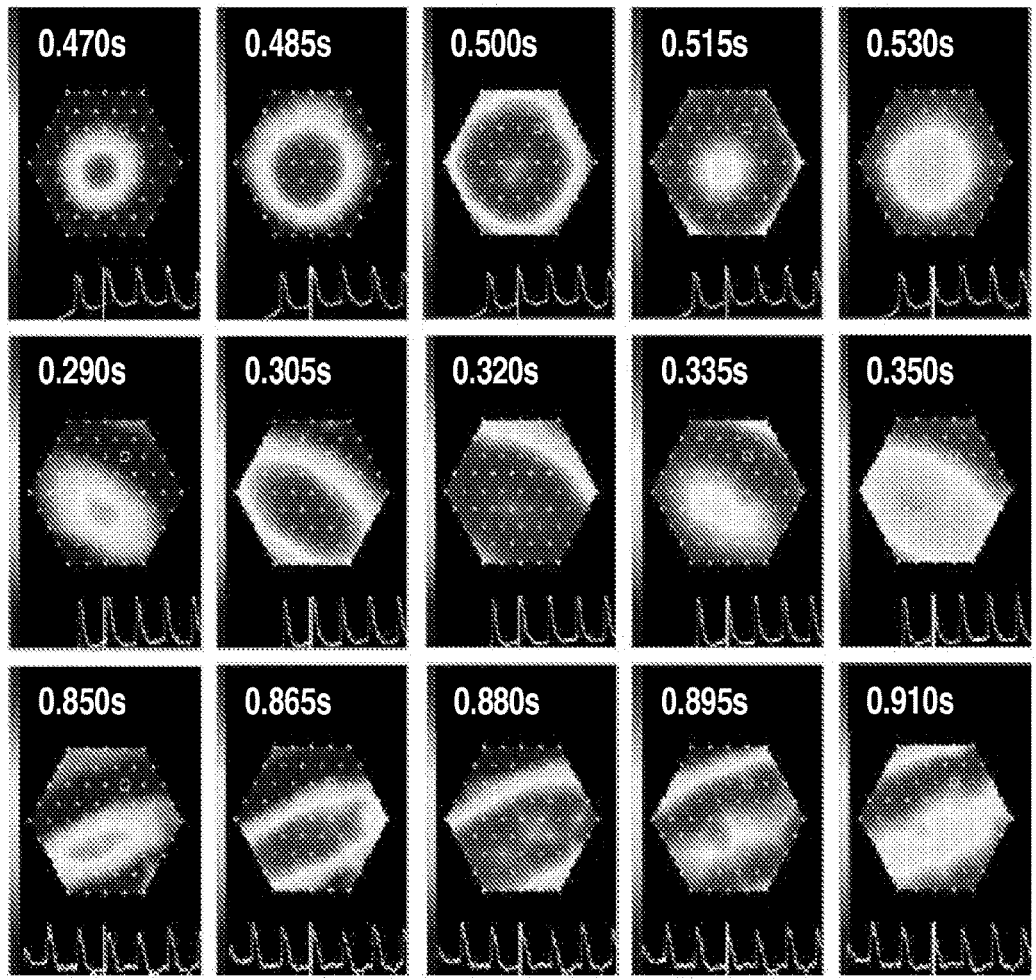
FIG. 4 depicts action potential wavefront propagation in paced tissues with different anisotropy ratios (AR). In this example, all tissues were stimulated with a point electrode in the center of the tissue. The optical signals were normalized by the action potential amplitude to represent the transmembrane voltage in color. For each frame, the gray scale bar on the left indicates the resting state with dark gray and the peak of the action potential with medium gray. The white trace on the bottom is from a recording made at the site marked by the white square. The top panels show the action potential wavefront propagation in an isotropic tissue (AR=1). The middle and bottom panels show the wavefront propagation in anisotropic tissues with AR=2 and AR=3, respectively.

Normal cardiac muscle has anisotropic action potential propagation, which is required for coordination of the spatiotemporal contraction of the heart. Anisotropy in the cardiac rhythm modulation tissue structure is required to properly couple with the anisotropic cardiac muscle of the heart and initiate action potential propagation in the appropriate direction. FIG. 4 illustrates action potential wavefront propagation in isotropic and anisotropic tissues. The anisotropy of the cardiac rhythm modulation tissue structure can be configured to control the direction of action potential propagation or the conduction velocity.

The anisotropy ratio (AR) is defined as the velocity of action potential propagation in the longitudinal direction divided by the transverse direction. The anisotropic engineered cardiac rhythm modulation tissue structure in FIG. 4 has an anisotropy ratio ranging from 1-3. The AR also controls conduction velocity. For example, in the case of the AV bypass, the AR of the cells on the bypass can be controlled to produce slower conduction (longer A-V delays) with lower ARs and faster conduction (shorter A-V delays) with higher ARs.

I. Photosensitive Cardiac Rhythm Modulation Systems

In one aspect, the present invention provides a photosensitive cardiac rhythm modulation system. The photosensitive cardiac rhythm modulation system comprises a cardiac rhythm modulation tissue structure as described herein. As used herein, a "photosensitive cardiac rhythm modulation tissue structure" is a biologically engineered tissue comprising a population of cardiac, e.g., pacemaker cells, expressing a photosensitive membrane transport mechanism, such as a light-gated ion channel or a light-driven ion pump. As used herein, a "photosensitive cardiac rhythm modulation system" is a photosensitive cardiac rhythm modulation tissue structure further comprising, for example a light source adapted to provide photostimulation to the cells, a sensor array, and a power generator.

Methods for fabricating a cardiac rhythm modulation tissue structure comprising cardiac cells, e.g., pacemaker cells, are generally described in PCT Publication No. WO 2008/051265, U.S. Provisional Application No. 61/249,870, U.S. Provisional Application No. 61/391,203, PCT/US11/024029, the entire contents of each of which are incorporated herein by reference. An exemplary embodiment of a method for fabricating a cardiac rhythm modulation tissue structure comprising genetically engineered cells (e.g., cells transfected with a photosensitive membrane transport mechanism) is depicted in FIG. 1. The methods generally include, providing a base layer; depositing a sacrificial polymer on the base layer, thereby generating a sacrificial polymer layer; depositing a flexible polymer layer that is more flexible than the base layer on the sacrificial polymer layer; seeding the genetically engineered cells expressing one or more photosensitive membrane transport mechanisms on the flexible polymer layer; culturing the cells to form a tissue structure; and releasing the flexible polymer layer from the base layer.

The base layer used in the compositions and methods of the invention is formed of a rigid or semi-rigid material, such as glass, plastic, metal, ceramic, or combinations thereof. In particular embodiments, the Young's modulus of the base material used to form the base layer is greater than 1 mega-pascal (MPa). The base layer material may also be transparent, facilitating observation. Examples of suitable base layer materials include polymethylmethacrylate, polystyrene, polyethylene terephthalate film, silicon wafer, and gold. In various embodiments, the base layer is a silicon wafer, a glass cover slip, a multi-well plate or a tissue culture plate.

The sacrificial polymer layer is deposited on the base layer, i.e., is placed or applied onto the base layer. Depositing may include, but is not limited to, spraying, dip casting, and spin-coating. The sacrificial polymer layer may be deposited on substantially the entire surface or only a portion of the surface of the base layer.

In one embodiment, spin-coating is used to deposit the sacrificial polymer layer on the base material. "Spin-coating" is a process wherein the base layer is mounted to a chuck under vacuum and is rotated to spin the base layer about its axis of symmetry while a liquid or semi-liquid substance, e.g. a polymer, is dripped onto the base layer. Centrifugal force generated by the spin causes the liquid or semi-liquid substance to spread substantially evenly across the surface of the base layer.

In one embodiment, the sacrificial polymer is a thermally sensitive polymer that can be melted or dissolved to release the flexible polymer layer. For example, linear non-cross-linked poly(N-Isopropylacrylamide) (PIPAAM), which is a solid when dehydrated or at about 37° C., wherein the polymer is hydrated, but relatively hydrophobic. When the temperature of the polymer is dropped to about 35° C. or less, wherein the polymer is hydrated, but relatively hydrophilic, the polymer liquefies, thereby releasing the patterned flexible polymer layer (Feinberg et al., *Science* 317:1366-1370, 2007).

In another embodiment, the sacrificial polymer becomes hydrophilic when the temperature is lowered, thereby releasing hydrophobic coatings. For example, the sacrificial polymer can be hydrated, cross-linked PIPAAM, which is hydrophobic at about 37° C. and hydrophilic at about 35° C. or less (e.g., about 35° C. to about 32° C.). In yet another embodiment, the sacrificial polymer is an electrically actuated polymer that becomes hydrophilic upon application of an electric potential and releases a hydrophobic structure coated thereon. Examples of such a polymer include poly (pyrrole)s, which are relatively hydrophobic when oxidized and hydrophilic when reduced. Other examples of polymers that can be electrically actuated include poly(acetylene)s, poly(thiophene)s, poly(aniline)s, poly(fluorene)s, poly(3-hexylthiophene), polynaphthalenes, poly(p-phenylene sulfide), and poly(para-phenylene vinylene)s. In another embodiment, the sacrificial polymer is a degradable biopolymer that can be dissolved to release a structure coated thereon. For example, the polymer (e.g., polylactic acid, polyglycolic acid, poly(lactic-glycolic) acid copolymers, or nylons) undergoes time-dependent degradation by hydrolysis or by enzymatic action (e.g., fibrin degradation by plasmin, collagen degradation by collagenase, fibronectin degradation by matrix metalloproteinase).

In one embodiment, the sacrificial polymer is an ultra-hydrophobic polymer with a surface energy lower than the flexible polymer layer adhered to it. In this case, mild mechanical agitation will "pop" the patterned flexible polymer layer off of sacrificial polymer layer. Examples of such a polymer include but are not limited to alkylsilanes (octadecyltrichlorosilane and isobutyltrimethoxysilane), fluoroalkylsilanes (tridecafluorotetrahydrooctyltrichlorosilane, trifluoropropyltrichlorosilane and heptadecafluorotetrahydrodecyltrichlorosilane), silicones (methylhydrosiloxane-dimethylsiloxane copolymer, hydride terminated polydimethylsiloxane, trimethylsiloxy terminated polydimethylsiloxane and diacetoxymethyl terminated polydimethylsiloxane), fluorinated polymers (polytetrafluoroethylene, perfluoroalkoxy and fluorinated ethylene propylene). For example, the base material can be a glass cover slip coated with a sacrificial polymer layer of PIPAAM.

A flexible polymer layer is applied to the sacrificial polymer layer by means described above for depositing the sacrificial polymer layer on the base layer. Suitable polymers include any medical grade biocompatible flexible polymer, such as polydimethylsiloxane (PDMS) and polyurethane. Thermoplastic or thermosetting polymers can be used to form the flexible polymer layer. Alternative non-degradable polymers include polyurethanes, silicone-urethane copolymers, carbonate-urethane copolymers, polyisoprene, polybutadiene, copolymer of polystyrene and polybutadiene, chloroprene rubber, polyacrylic rubber (ACM, ABR), fluorosilicone rubber (FVMQ), fluoroelastomers, perfluoroelastomers, tetrafluoro ethylene/propylene rubbers (FEPM) and ethylene vinyl acetate (EVA). Biopolymers, such as collagens, elastins, and other extracellular matrix proteins, are also suitable. Appropriate biodegradable elastomers include hydrogels, elastin-like peptides, polyhydroxyalkanoates and poly(glycerol-sebecate). Suitable non-elastomer, biodegrable polymers include polylactic acid, polyglycolic acid, and polylactic glycolic acid copolymers.

In one embodiment, the flexible polymer layer comprises polydimethylsiloxane (PDMS). Thickness of the PDMS layer can be controlled by the viscosity of the prepolymer and by the spin-coating speed, ranging from 14 to 60 μm thick after cure. The viscosity of the prepolymer increases as the cross-link density increases. This change in viscosity between mixing and gelation can be utilized to spin-coat different thicknesses of flexible polymer layers. Alternatively the spin-coating speed can be increased to create thinner polymer layers. After spin-coating, the resulting polymer scaffolds are either fully cured at room temperature (generally, about 22° C.) or at 65° C.

Next, the flexible polymer layer is uniformly or selectively patterned with engineered surface chemistry to elicit (or inhibit) cell growth and function. The engineered surface chemistry is prepared, for example, by exposure of the flexible polymer layer to ultraviolet radiation or ozone, or via acid or base wash or plasma treatment to increase the hydrophilicity of the surface.

A specific biopolymer (or combination of biopolymers) may be selected to recruit different integrins, or an engineered surface chemistry may be fabricated on the flexible polymer layer to enhance or inhibit cell and/or protein adhesion. The specific type of biopolymer used and geometric spacing of the patterning will vary with the application. In one embodiment, the engineered surface chemistry comprises a biopolymer, such as an extrecalular matric (ECM) protein, to pattern specific cell types. The ECM may comprise fibronectin, laminin, one or more collagens, fibrin, fibrinogen, or combinations thereof. In one embodiment, the ECM is not uniformly distributed on the surface of the flexible polymer, but rather is patterned spatially using techniques including, but not limited to, soft lithography, self assembly, vapor deposition, and photolithography.

"Biopolymer" refers to any proteins, carbohydrates, lipids, nucleic acids or combinations thereof, such as glycoproteins, glycolipids, or proteolipids. Examples of suitable biopolymers that may be used for substrate functionalization include, without limitation:

(a) extracellular matrix proteins to direct cell adhesion and function (e.g., collagen, fibronectin, laminin, vitronectin, or polypeptides (containing, for example the well known-RGD-amino acid sequence));

(b) growth factors to direct specific cell type development cell (e.g., nerve growth factor, bone morphogenic proteins, or vascular endothelial growth factor);

(c) lipids, fatty acids and steroids (e.g., glycerides, non-glycerides, saturated and unsaturated fatty acids, cholesterol, corticosteroids, or sex steroids);

(d) sugars and other biologically active carbohydrates (e.g., monosaccharides, oligosaccharides, sucrose, glucose, or glycogen);

(e) combinations of carbohydrates, lipids and/or proteins, such as proteoglycans (protein cores with attached side chains of chondroitin sulfate, dermatan sulfate, heparin, heparan sulfate, and/or keratan sulfate); glycoproteins (selectins, immunoglobulins, hormones such as human chorionic gonadotropin, Alpha fetoprotein or Erythropoietin (EPO)); proteolipids (e.g., N-myristoylated, palmitoylated and prenylated proteins); and glycolipids (e.g., glycoglycerolipids, glycosphingolipids, or glycophosphatidylinositols); (f) biologically derived homopolymers, such as polylactic and polyglycolic acids and poly-L-lysine;

(g) nucleic acids (e.g., DNA or RNA);

(h) hormones (e.g., anabolic steroids, sex hormones, insulin, or angiotensin);

(i) enzymes (e.g., oxidoreductases, transferases, hydrolases, lyases, isomerases, ligases; examples: trypsin, collegenases, or matrix metalloproteinases);

(j) pharmaceuticals (e.g., beta blockers, vasodilators, vasoconstrictors, pain relievers, gene therapy, viral vectors, or anti-inflammatories);

(k) cell surface ligands and receptors (e.g., integrins, selectins, or cadherins); and (l) cytoskeletal filaments and/or motor proteins (e.g., intermediate filaments, microtubules, actin filaments, dynein, kinesin, or myosin).

In one embodiment of the invention, a photosensitive cardiac rhythm modulation tissue structure is engineered using alternating high density lines of ECM protein with either low density ECM protein or a chemical that prevents protein adhesion (e.g., Pluronics F127). The spacing of these lines is typically 20 µm width at 20 µm spacing, (Feinberg, Science 317:1366-1370, 2007), however, the width and spacing may be altered to change the alignment. Changes in alignment in turn affect anisotropy and anisotropy ratio of the action potential propagation. The width and spacing of the ECM lines may be varied over the range from about 0.1 µm to about 1000 µm, from about 1 µm to about 500 µm, from about 1 µm to 250 µm, from about 1 µm to 100 µm, from about 1 µm to 90 µm, from about 1 µm to 80 µm, from about 1 µm to 70 µm, from about 1 µm to 60 µm, from about 1 µm to 50 µm, from about 1 µm to 40 µm, from about 1 µm to 30 µm, from about 1 µm to 20 µm, from about 1 µm to 10 µm, from about 2 µm to 100 µm, from about 2 µm to 90 µm, from about 2 µm to 80 µm, from about 2 µm to 70 µm, from about 2 µm to 60 µm, from about 2 µm to 50 µm, from about 2 µm to 40 µm, from about 2 µm to 30 µm, from about 2 µm to 20 µm, from about 2 µm to 10 µm, from about 1 µm to 100 µm, from about 5 µm to about 100 µm, from about 5 µm to about 90 µm, from about 5 µm to about 80 µm, from about 5 µm to about 70 µm, from about 5 µm to about 60 µm, from about 5 µm to about 50 µm, from about 5 µm to about 40 µm, from about 5 µm to about 30 µm, from about 5 µm to about 20 µm, and from about 5 µm to about 20 µm. The width and spacing of the ECM lines can be equivalent or disparate. For example, both the width and spacing can be about 0.1, about 0.2, about 0.25, about 5, about 0.75, about 1, about 2, about 3, about 4, about 5, about 6, about 7, about 8, about 9, about 10, about 11, about 12, about 13, about 14, about 5, about 16, about 17, about 18, about 19, about 20 µm, or the width can be about 0.1, about 0.2, about 0.25, about 5, about 0.75, about 1, about 2, about 3, about 4, about 5, about 6, about 7, about 8, about 9, about 10 µm and the spacing about 1, about 2, about 3, about 4, about 5, about 6, about 7, about 8, about 9, about 10, about 11, about 12, about 13, about 14, about 5, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 µm, or conversely, the width can be about 1, about 2, about 3, about 4, about 5, about 6, about 7, about 8, about 9, about 10, about 11, about 12, about 13, about 14, about 5, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 µm and the spacing about 0.1, about 0.2, about 0.25, about 5, about 0.75, about 1, about 2, about 3, about 4, about 5, about 6, about 7, about 8, about 9, about 10 µm. Typically the patterned ECM lines are parallel to one another, but they may also be at angles to one another at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90°. In one embodiment, the patterned ECM lines are parallel to one another at angles ranging from about 1° to about 90°. In another embodiment, he patterned ECM lines are parallel to one another at angles ranging from about 5° to about 45°. The angle between the patterned lines of ECM protein controls the directionality of action potential propagation. The width of the cardiac rhythm modulation tissue structure itself can be tapered to control the direction of action potential propagation. For example, a wide cardiac rhythm modulation tissue structure strip that tapers to a narrow strip will propagate an action potential from the wide to the narrow direction, but not in the opposite direction. Values and ranges intermediate to the above-recited values and ranges are also contemplated by the present invention.

Photosensitive cardiac rhythm modulation tissue structures can be specifically configured for epicardial or endocardial attachment. The cardiac rhythm modulation tissue structure is constructed in an appropriate size, shape and architecture so that it will functionally connect with the epicardium or endocardium. Functional attachment can be demonstrated by the formation of adherens and gap junctions between the cells of the biological cardiac rhythm structure and the cells of epicardium or endocardium. These structures couple the biological cardiac rhythm structure to the cardiac tissue mechanically and electrically.

Photosensitive cardiac rhythm modulation tissue structures can also be specifically configured to generate an electrical impulse that induces an action potential through the attached cardiac tissue. Optical mapping can be used to assess whether the photosensitive cardiac rhythm modulation tissue structure is functionally attached to the epicardium or endocardium.

Once patterning of the flexible polymer surface is completed, the genetically engineered cells described in section II below are seeded onto the flexible polymer layer in an appropriate culture medium, and are cultured to form a tissue. Any appropriate cell culture method may be used to establish the tissue on the polymer surface. The seeding density of the cells will vary depending on the cell size and cell type, but can easily be determined by methods known in the art. In one embodiment, cardiac myocytes are seeded at a density of between about $1\times10^5$ to about $6\times10^5$ cells/cm$^2$, or at a density of about $1\times10^4$, about $2\times10^4$, about $3\times10^4$, about $4\times10^4$, about $5\times10^4$, about $6\times10^4$, about $7\times10^4$, about $8\times10^4$, about $9\times10^4$, about $1\times10^5$, about $1.5\times10^5$, about $2\times10^5$, about $2.5\times10^5$, about $3\times10^5$, about $3.5\times10^5$, about $4\times10^5$, about $4.5\times10^5$, about $5\times10^5$, about $5.5\times10^5$, about $6\times10^5$, about $6.5\times10^5$, about $7\times10^5$, about $7.5\times10^5$, about $8\times10^5$, about $8.5\times10^5$, about $9\times10^5$, about $9.5\times10^5$, about $1\times10^6$, about $1.5\times10^6$, about $2\times10^6$, about $2.5\times10^6$, about $3\times10^6$, about $3.5\times10^6$, about $4\times10^6$, about $4.5\times10^6$, about $5\times10^6$, about $5.5\times10^6$, about $6\times10^6$, about $6.5\times10^6$, about $7\times10^6$, about $7.5\times10^6$, about $8\times10^6$, about $8.5\times10^6$, about $9\times10^6$, or about $9.5\times10^6$. Values and ranges intermediate to the above-recited values and ranges are also contemplated by the present invention.

In one embodiment, cardiac myocytes are co-cultured with neurons to prepare innervated engineered tissue comprising pacemaking cells, and/or to accelerate the maturation of the cultured cells as described in U.S. Provisional Application Nos. 61/306,736 and 61/391,203, the entire contents of each of which are incorporated herein by reference. In another embodiment, cardiac myocytes are co-cultured with photosensitive tissues and/or cells, such as those derived from retina or the chromatophores of invertebrates and lower vertebrates, e.g., cephalopods, amphibians, fish, reptiles, and crustaceans.

Once seeded, cells are allowed to attach and form a two-dimensional tissue on the flexible polymer surface. When the required level of cell coverage on the polymer surface is achieved, the flexible polymer layer can be cut into a desired shape and size and be removed from the sacrificial polymer layer, producing a free-standing photosensitive cardiac rhythm modulation tissue structure comprising cardiac cells genetically engineered to respond to light thereby stimulating or to inhibiting action potentials.

The cell patterning of a photosensitive cardiac rhythm modulation tissue structure can be precisely controlled. In various embodiments the photosensitive cardiac rhythm modulation tissue structure can comprise a single continuous homogenous layer of excitable cells or multiple discrete regions, such as fibers or threads, of excitable cells. The width of fibers or threads can be altered to manipulate the strength of electrical conductivity through the photosensitive cardiac rhythm modulation tissue structure.

A specific shape (e.g., triangle, oval, teardrop) can be cut in the flexible polymer film using a scalpel, punch, die, laser, photolithography, or other appropriate method. The sacrificial layer is then dissolved or actuated to release the flexible polymer from the rigid base as described above. The cut-out shape then floats free or is gently peeled away from the sacrificial layer. In some embodiments, the cardiac cells are aligned unidirectionally along the long axis of the photosensitive cardiac rhythm modulation tissue structure. The degree of cellular alignment, and thus anisotropy, can be precisely controlled and optimized for the shape and/or functional requirements of the graft by manipulating the engineered surface chemistry. A directional, polarizing current can also be created by controlling the cellular architecture of the photosensitive cardiac rhythm modulation tissue structure. For example, a zone of non-excitable cells can be incorporated into one or more regions of the cardiac rhythm modulation tissue structure to effect a block of the polarizing current in a particular direction. By controlling the positioning of the non-excitable cells one can control the direction of the polarizing current produced by the cardiac rhythm modulation tissue structure. Any non-excitable cells may be used to effect a block of the polarizing current. Such non-excitable cells include, but are not limited to, human cardiac fibroblasts, endothelial cells and vascular smooth muscle cells.

Figure 6A:
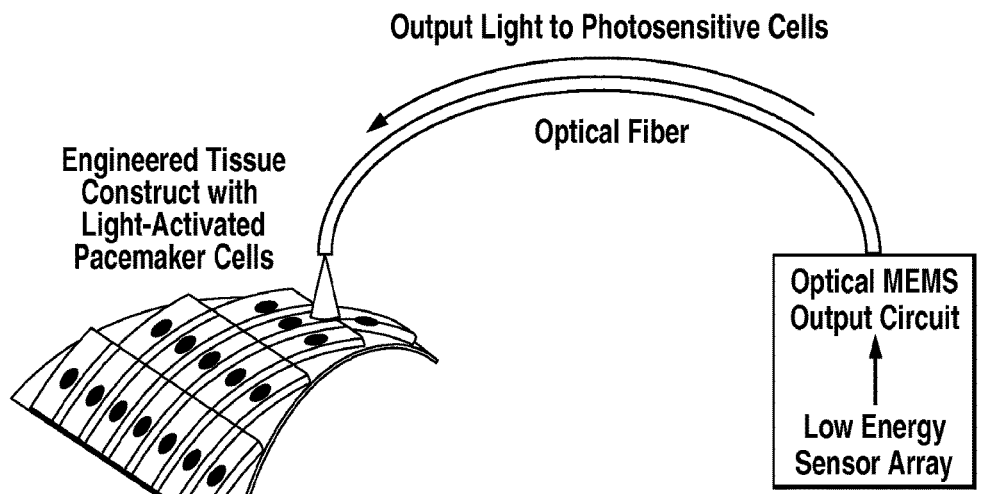
FIG. 6A depicts a basic optical pacemaker controlled by a sensor array. Light-activated pacemaker cells are stimulated by light transmitted from a light source through an optical fiber. The pacemaker cells will function as a pacemaker or defibrillator depending on the heterologous ion channels present.
Figure 6B:
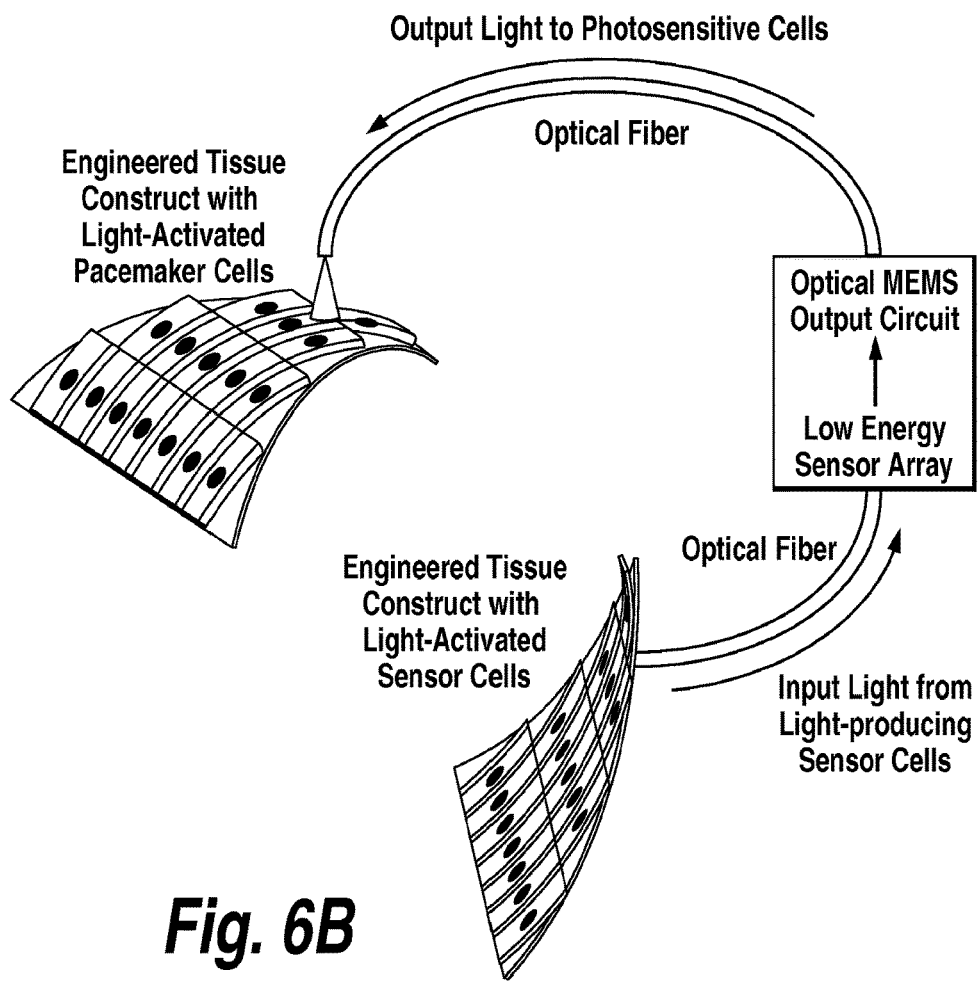
FIG. 6B depicts an optical pacemaker controlled by optical cellular sensor. Light-activated pacemaker cells are stimulated by light provided by light-producing cells and transmitted through an optical fiber.
Figure 7:
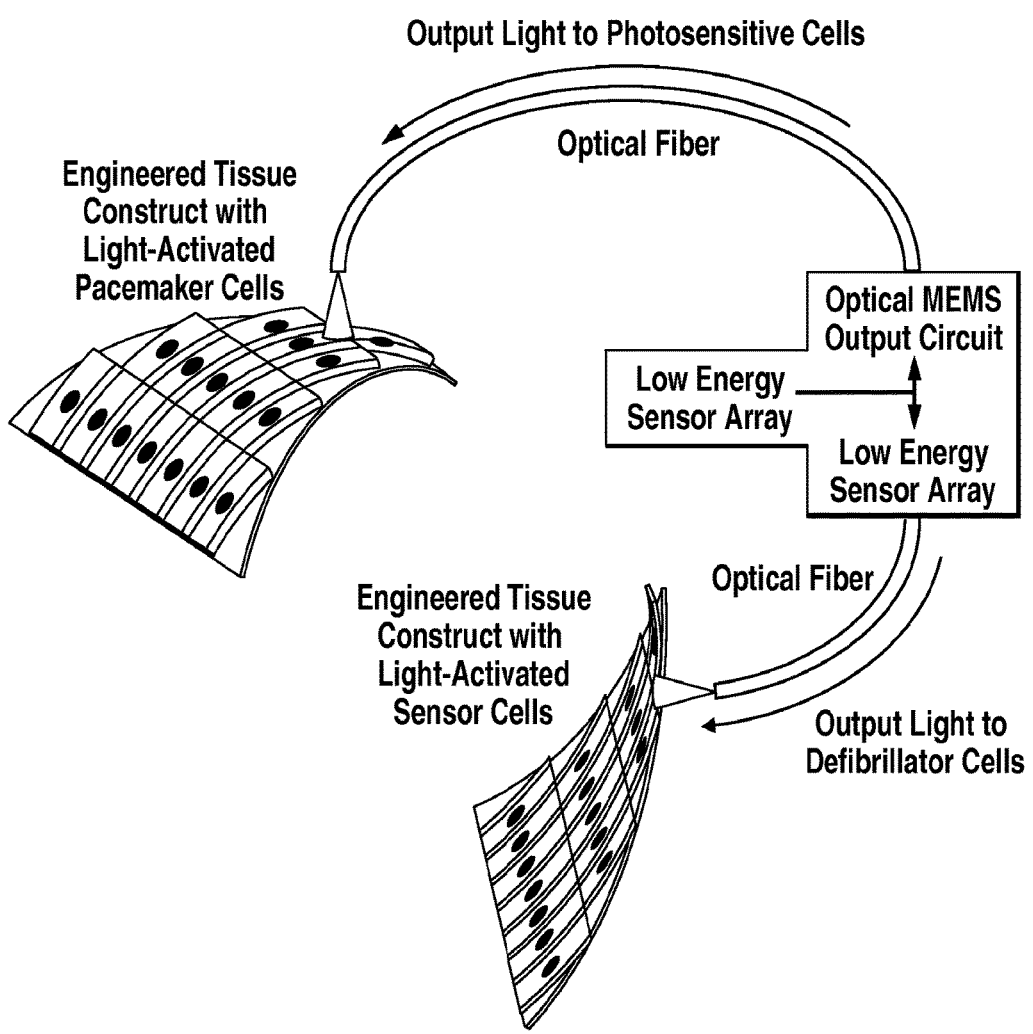
FIG. 7 depicts an embodiment of an optical pacemaker/ defibrillator. Light of the appropriate wavelength is transmitted through optical fibers to either light-activated or light-silenced pacemaker cells to regulate cardiac function.

The photosensitive cardiac rhythm modulation tissue structures of the invention may be coupled to or combined with controlling components comprising one or more of a sensor, generator, and light source, as shown in FIGS. 6 and 7, thus forming photosensitive cardiac rhythm modulation systems. For example, the pacemaker or defibrillator function of the photosensitive cardiac rhythm modulation system can be actuated by photostimulation from an integrated fiber optic microelectromechanical systems (MEMS) device. The sensor analyzes heart rate and rhythm and signals the generator when a correction in beat or rhythm is necessary. The generator provides power for the sensor and the light source. Only very small amounts of light are required, reducing power consumption and allowing the use of very small generators, e.g., batteries. The light source produces light of a specific wavelength(s) for selective stimulation or silencing of action potentials within the biological cardiac rhythm modulation structure. For example, blue light wavelengths (approximately 445-490 nm, preferably 470-475 nm) can be used to activate ChR2 and stimulate action potentials and yellow light wavelengths (approximately 573-613 nm, preferably 575 to 625 nm) can be used to activate NpHR and silence action potentials. The light source can comprise high intensity light-emitting diodes (LED), a diode laser, or other light source coupled to an optical fiber. In exemplary embodiments, a low-power or ultra-low-power sensor array may be adapted to function as a light source, e.g., in conjunction with a fiber optic delivery scheme. In further exemplary embodiments, a chemiluminescent light source such as bioengineered light source may be utilized. Thus, e.g., photocytes may be integrated with optical relay and/or optical switching element to provide photostimulation.

The light source may be tethered to an external power source or powered by an implanted battery pack. Commercially available ultra-compact fiber-coupled diode laser modules, such as the FIBERTEC$^{II\text{TM}}$ (Blue Sky Research, Milpitas, Calif.) modules, are suitable light sources. The light source may advantageously be controlled using a microelectromechanical system (MEMS) system and associated fiber optics. MEMS systems may include, e.g., MEMS-driven optical switches or digital micromirror devices (DMD) (for digital light processing). In exemplary embodiments, the light source may provide programmable high spatial and temporal resolution multipoint photostimulation of the photosensitive tissue, e.g., using a guided laser. Spatial resolution may be, e.g., on the micron level and temporal resolution may be e.g., on the millisecond level. Thus, a guided laser could readily focus on and independently stimulate, e.g., either of two neighboring muscular actuators (gaps in tissue continuity may be used to establish discrete regions for photostimulation). In exemplary embodiments, an external light source may be used to provide photostimulation. Thus, in on embodiment, the light source may comprise a tissue-penetrating infrared light for transthoracic photostimulation.

II. Cells Expressing Photosensitive Membrane Transport Mechanisms

The photosensitive cardiac rhythm modulation tissue structures described above may comprise any suitable electrically excitable cell including, but not limited to, cells derived from a sinoatrial or an atrioventricular node, cells derived from the cardiac conduction system, and cardiac progenitor cells for the nodes and conduction system. Preferred cells are cardiac myocytes. Any genetically engineered cells that possess the required electrical excitation or pacemaker properties are also appropriate. These include, but are not limited to, embryonic stem cells, induced pluripotent stem (iPS) cells, adult mesenchymal stem cells, adult cardiac resident stem cells, and other adult stem cells (e.g., hematopoietic cells, fat cells). In one embodiment, cells suitable for use in a photosensitive cardiac rhythm modulation tissue structures are pacing cells from a stable cell line, e.g., an iPS cell line, generated by transfecting pacing cells with a photosensitive membrane transport mechanism. The cells may advantageously be suitable for excitation-contraction (EC) coupling relative to endogenous cardiac muscle tissue.

In one embodiment, cells suitable for use in compositions and methods of the present invention are those described PCT/US09/060224, titled "Tissue Engineered Myocardium and Methods of Production and Uses Thereof", filed on Oct. 9, 2009, the entire contents of which are expressly incorporated herein by reference.

Cells from any species that do not cause an adverse immune reaction in the recipient may be used. In various embodiments, the excitable cells are syngeneic cells, human cells, allogeneic cells or autologous cells. In a preferred embodiment, the cells are human cardiac myocytes.

The cells are genetically engineered to be photosensitive. For example, these cells are genetically engineered to express a photosensitive membrane transport mechanism. As used herein, the term "photosensitive membrane transport mechanism" refers to an ion channel or ion transporter protein that is sensitive to a specific wavelength(s) of light and can be used to generate or silence action potentials in cells expressing these proteins. As a result, the biological cardiac rhythm modulation tissue structures become photosensitive and can be regulated by light stimulation. Through the use of specific ion channel or ion transporter proteins, action potentials may be stimulated (to restore regular beating) or silenced (to inhibit defibrillation).

Heterologously expressed microbial opsins can be used to control membrane potential. These include channelrhodopsins, halorhodopsins, and bacteriorhodopsins (reviewed in J. P. Klare, et al., *Result. Probl. Cell. Differ.* 45: 73-122, 2008). For example, channel rhodopsin-1 (ChR1), a light-gated proton channel, and channelrhodopsin-2 (ChR2), a light-activated cation channel naturally expressed by *Chlamydomonas reinhardtii*, may be used.

The N-terminal 315 amino acids of ChR2 compose an ion channel with light-gated conductance. ChR2 has been expressed stably in mammalian neurons, where it is capable of driving neuronal depolarization. Upon exposure to blue light, ChR2 expressed in genetically engineered neurons rapidly stimulates neuronal spiking and creates action potentials. (E S Boyden, et al., *Nat. Neurosci.* 8: 1263-1268, 2005). VChR1 from *Volvox carteri*, exhibits an action spectrum with two maxima, 531 nm and 589 nm, which are red-shifted with respect to the absorption maximum of ChR2 (approximately 470 nm) (F. Zhang, et al., *Nat. Neurosci.* 11: 631-633, 2008). Halorhodopsins include NpHR, which is naturally expressed by *Natronomonas pharaonic*. NpHR is a high-speed hyperpolarizing chloride ion pump responsive to yellow light. When expressed in genetically engineered neurons, NpHR inhibits action potentials in response to yellow light. (F. Zhang, et al., *Nature* 446: 633-639, 2007). Bacteriorhodopsin is stimulated by green light, wavelength of 500-650 nm, with absorption maximum at 568 nm.

When expressed in cells, bacterial opsins such as ChR2, VChR1 and NpHR provide complementary tools for regulating the frequency and rhythm of heartbeat. For example, in one embodiment of the invention, cells are genetically engineered to express ChR2 to stimulate action potentials in response to blue light. These cells function as a pacemaker. In another embodiment, cells are genetically engineered to express NpHR, to inhibit action potentials and propagation of action potentials. These cells function as a defibrillator.

The gene sequences for ChR1, VChR1, ChR2, and NpHR are known in the art and may be found in, for example, GenBank Reference Nos. GI:159481916, GI:159487988, GI:159481998, GI:167650745, GI:167650741, GI:76800655, (the contents of each of which are incorporated herein in their entirety), and heterologous expression has been reported for each of these opsin genes (E S Boyden, et al., *Nat. Neurosci.* 8: 1263-1268, 2005; F. Zhang, et al., *Nat. Neurosci.* 11: 631-633, 2008; F. Zhang, et al., *Nature* 446: 633-639, 2007).

In one embodiment, the cells for use in a cardiac rhythm modulation system are transfected with the photosensitive membrane transport mechanism, e.g., an opsin gene, prior to formation of cardiac rhythm modulation tissue structures. In another embodiment, the cells for use in a cardiac rhythm modulation tissue structure are transfected with the photosensitive membrane transport mechanism, e.g., an opsin gene, after growth on the flexible polymer surface. In yet another embodiment, cardiac cells are transfected with a photosensitive membrane transport system in situ, i.e., while the cells are present within the heart of a human subject.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAM-FECT™ (OZ Biosciences, France) and the like), or electroporation (e.g., in vivo electroporation). Suitable methods for transforming or transfecting host cells can be found in Sambrook, et al. (Molecular Cloning: A Laboratory Manual. 2nd, ed., Cold Spring harbor Laboratory, Cold Spring Harbor Laboratory Press, Cold Spring Harbor, N.Y., 1989), and other laboratory manuals.

Any appropriate method known in the art may be used to transfect cells with a photosensitive membrane transport mechanism. Standard methods include transfection with viral or nonviral vector systems, electroporation, and microinjection. For example, in one embodiment, substrate-mediated transfection as described in, for example, Ziauddin and Sabatini (*Nature* (2001) 3:411), Houchin-Ray, et al. (*Mol Thera* (2007) 15(4):705-12), Jang, et al. (*J Biomed Mater Res A.* (200) 77(1):50-8, and WO/2006/031800, the entire contents of which are incorporated herein by reference, may be used to transfect cells. In another embodiment, patterned surface-mediated transfection as described in, for example, Hu, et al. (*Gene Ther.* (2007) 14(11):891-901), Lei, et al. (*Biomaterials.* (2009) 30(22):3790-9), and Stachelek, et al. (*Gene Ther.* (2004) 11(1):15-24), the entire contents of which are incorporated herein by reference, may be used to transfect cells.

Viral and nonviral vector systems can be designed using known methods to combine the elements necessary for directing transcription, translation, or both, of the nucleic acid encoding a photosensitive membrane transport mechanism in a cell. Methods known in the art can be used to construct expression constructs having the protein coding sequence operably linked with appropriate transcriptional/translational control signals. These methods are fully described in a number of laboratory manuals including *Current Protocols in Molecular Biology*, Online ISSN: 1934-3647, John Wiley & Sons, NY, 2010; *Gene Transfer: Delivery and Expression of DNA And RNA, A Laboratory Manual*, Theodore Friedmann and John Rossi, Cold Spring Harbor Laboratory Press, 2006; *Molecular Cloning: A Laboratory Manual*, 3rd Ed., J. Sambrook and D. Russell, Cold Spring Harbor Laboratory Press, 2001; Techniques for the formation of vectors or virions are generally described in "Working Toward Human Gene Therapy," Chapter 28 in Recombinant DNA, 2nd Ed., Watson, J. D. et al., eds., New York: Scientific American Books, pp. 567-581 (1992). An overview of suitable viral vectors or virions is provided in Wilson, J. M., Clin. Exp. Immunol. 107(Suppl. 1):31-32 (1997), as well as Nakanishi, M., Crit. Rev. Therapeu. Drug Carrier Systems 12:263-310 (1995); Robbins, P. D., et al., Trends Biotechnol. 16:35-40 (1998); Zhang, J., et al., Cancer Metastasis Rev. 15:385-401 (1996); and Kramm, C. M., et al., Brain Pathology 5:345-381 (1995). Such vectors may be derived from viruses that contain RNA (Vile, R. G., et al., Br. Med Bull. 51:12-30 (1995)) or DNA (Ali M., et al., Gene Ther. 1:367-384 (1994)).

Examples of viral vector systems particularly suitable for use in the in vivo transfection of cardiac muscle cells with a photosensitive membrane transport system, include the following: retroviruses (Vile, R. G., supra; U.S. Pat. Nos. 5,741,486 and 5,763,242); adenoviruses (Brody, S. L., et al., Ann. N.Y. Acad. Sci. 716: 90-101 (1994); Heise, C. et al., Nat. Med. 3:639-645 (1997)); adenoviral/retroviral chimeras (Bilbao, G., et al., FASEB J. 11:624-634 (1997); Feng, M., et al., Nat. Biotechnol. 15:866-870 (1997)); adeno-associated viruses (Flotte, T. R. and Carter, B. J., Gene Ther. 2:357-362 (1995); U.S. Pat. No. 5,756,283); herpes simplex virus I or II (Latchman, D. S., Mol. Biotechnol. 2:179-195 (1994); U.S. Pat. No. 5,763,217; Chase, M., et al., Nature Biotechnol. 16:444-448 (1998)); parvovirus (Shaughnessy, E., et al., Semin Oncol. 23:159-171 (1996)); reticuloendotheliosis virus (Donburg, R., Gene Therap. 2:301-310 (1995)). Extrachromosomal replicating vectors may also be used for the in vivo transfection of cardiac muscle cells with a photosensitive membrane transport system. Such vectors are described in, for example, Calos, M. P. (1996) Trends Genet. 12:463-466, the entire contents of which are incorporated herein by reference. Other viruses that can be used as vectors for gene delivery include poliovirus, papillomavirus, vaccinia virus, lentivirus, as well as hybrid or chimeric vectors incorporating favorable aspects of two or more viruses (Nakanishi, M. (1995) Crit. Rev. Therapeu. Drug Carrier Systems 12:263-310; Zhang, J., et al. (1996) Cancer Metastasis Rev. 15:385-401; Jacoby, D. R., et al. (1997) Gene Therapy 4:1281-1283). An AAV2/5 or AAV2/8 vector, as described in, for example, U.S. Pat. No. 7,056,502, (the entire contents of which are incorporated herein by reference) may also be used.

For in situ transfection of cardiac cells, a vector system targeting cardiac cells, such as an adeno-associated viral (AAV) system as described in, for example, U.S. Patent Applications 20090209631 and 20080263691, or a non-viral vector system as described in, for example, U.S. Pat. No. 6,436,907, U.S. Patent Application 20060199778, or U.S. Pat. No. 6,379,966 may also be used. The entire contents of all of the patents and application are incorporated herein by reference.

In another embodiment, cells are transfected with a lentivirus as described in T. Sakoda, et al., *J Mol Cell Cardiol* 31: 2037-47, 1999, and in *Lentivirus Gene Engineering Protocols 2nd Ed.*, Maurizio Federico, *Methods in Molecular Biology* Series, Humana Press, 2009.

The vector may include one or more promoters or enhancers, the selection of which will be known to those skilled in the art. Suitable promoters include, but are not limited to, the retroviral long terminal repeat (LTR), the SV40 promoter, the human cytomegalovirus (CMV) promoter, and other viral and eukaryotic cellular promoters known to the skilled artisan. In one embodiment, a suitable promoter is a cardiac-specific promoter, such as, but not limited to, the myosin light chain-2 promoter (Franz et al., 1994; Kelly et al., 1995), the alpha actin promoter (Moss et al., 1996), the troponin 1 promoter (Bhaysar et al, 1996); the Na+/Ca 2+ exchanger promoter (Barnes et al., 1997), the dystrophin promoter (Kimura et al., 1997), the creatine kinase promoter (Ritchie, M. E., 1996), the alpha7 integrin promoter (Ziober & Kramer, 1996), the brain natriuretic peptide promoter (LaPointe et al, 1996) and the alpha B-crystallin/small heat shock protein promoter (Gopal-Srivastava, R., 1995), alpha myosin heavy chain promoter (Yamauchi-Takihara et al., 1989) and the ANF promoter (LaPointe et al., 1988).

Guidance in the construction of vectors and the introduction thereof into a subject for therapeutic purposes may be obtained in the above-referenced publications, as well as in U.S. Pat. Nos. 5,631,236, 5,688,773, 5,691,177, 5,670,488, 5,529,774, 5,601,818, and PCT Publication No. WO 95/06486, the entire contents of which are incorporated herein by reference.

Following DNA transfer, the cells are screened to confirm expression and function of the exogenous gene encoding a photosensitive membrane transport mechanism using methods routine to one of ordinary skill in the art. For example, screening may include patch-clamp analysis to confirm the generation of action potentials, that such action potentials are induced by an opsin, and/or to quantify the transmembrane current, e.g., conduction velocity, duration, action potential morphology, generated by the opsin, optical mapping of cells, which when stained with a voltage-sensitive membrane dye, e.g., R11237, can be used to interpret subtle changes in fluorescence corresponding directly to changes in transmembrane potential, thus maintaining both spatial and temporal information about the cells, and ion channel expression by staining with e.g., β-tubulin III, atrial naturitic peptide, Sca-1, myosin, adrenergic receptors and/or muscarinic receptors (see, for example, Example 1, below).

III. In Vivo Uses of Photosensitive Cardiac Rhythm Modulation Tissue Structures and/or Photosensitive Cardiac Rhythm Modulation Systems The photosensitive cardiac rhythm modulation tissue structures and photosensitive cardiac rhythm modulation systems described above, which are capable of transducing or inhibiting an action potential in response to light of a specific wavelength, may be transplanted in vivo to regulate heart beat and heart rhythm. Photosensitive cardiac rhythm modulation tissue structures and systems with cells engineered to stimulate action potentials will function as pacemakers. Photosensitive cardiac rhythm modulation tissue structures and systems with cells engineered to inhibit action potentials will function as defibrillators. Photosensitive cardiac rhythm modulation tissue structures and systems may be used alone or in combination, as they are stimulated differentially by discrete wavelengths of light. When the photosensitive cardiac rhythm modulation tissue structures contact the host tissue, adherens and gap junctions develop that electrically connect the photosensitive cardiac rhythm modulation tissue structures with cells of the host tissue and allow pacemaker or defibrillator function. As used herein, the term "contacting" with reference to methods of treating cardiac dysfunction in a subject in need thereof, refers to implanting, layering, embedding, covering, placing, or enveloping the cardiac tissue of the subject with a photosensitive cardiac rhythm modulation tissue structure or system.

The exact size and shape of the photosensitive cardiac rhythm modulation tissue structure is species and patient specific. For example, for in vivo testing in a rat heart, the photosensitive cardiac rhythm modulation tissue structure may only be approximately 10 mm$^2$. In other embodiments, the size of the photosensitive cardiac rhythm modulation tissue structure can be about 0.1 mm$^2$, 0.2 mm$^2$, 0.5 mm$^2$, 1 mm$^2$, 2 mm$^2$, 3 mm$^2$, 4 mm$^2$, 5 mm$^2$, 6 mm$^2$, 7 mm$^2$, 8 mm$^2$, 9 mm$^2$, 10 mm$^2$, 11 mm$^2$, 12 mm$^2$, 13 mm$^2$, 14 mm$^2$, 15 mm$^2$, 16 mm$^2$, 17 mm$^2$, 18 mm$^2$, 19 mm$^2$, 20 mm$^2$, 21 mm$^2$, 1 mm$^2$, 22 mm$^2$, 23 mm$^2$, 24 mm$^2$, 25 mm$^2$, 26 mm$^2$, 27 mm$^2$, 28 mm$^2$, 29 mm$^2$, 30 mm$^2$, 31 mm$^2$, 32 mm$^2$, 33 mm$^2$, 34 mm$^2$, 35 mm$^2$, 36 mm$^2$, 37 mm$^2$, 38 mm$^2$, 39 mm$^2$, or about 40 mm$^2$. In yet other embodiments, the size of the MTF may range from about 0.1 mm$^2$ to 30 mm$^2$, 0.2 mm$^2$ to 30 mm$^2$, 0.5 mm$^2$ to 30 mm$^2$, 1 mm$^2$ to 30 mm$^2$, 2 mm$^2$ to 30 mm$^2$, 3 mm$^2$ to 30 mm$^2$, 4 mm$^2$ to 30 mm$^2$, 5 mm$^2$ to 30 mm$^2$, 6 mm$^2$ to 30 mm$^2$, 7 mm$^2$ to 30 mm$^2$, 8 mm$^2$ to 30 mm$^2$, 9 mm$^2$ to 30 mm$^2$, or about 10 mm$^2$ to 30 mm$^2$. For an adult human, the photosensitive cardiac rhythm modulation tissue structure is typically about 1, 1.5, 2, 2.5, 3, 3.5, 4, 4.5, or 5 cm in length for a square or rectangular shape or about 0.1, 0.2, 0.3, 0.4, 0.5, 0.6, 0.7, 0.8, 0.9, 1, 1.25, 1.5, 1.75, 2, 2.25, 2.5, 2.75, or about 3 cm in diameter for a circular shape. Suitable surface areas for the photosensitive cardiac rhythm modulation tissue structure can range from about 1 to 106 mm$^2$, about, 5 to 106 mm$^2$, 10 to 106 mm$^2$, 20 to 106 mm$^2$, 30 to 106 mm$^2$, 40 to 106 mm$^2$, 50 to 106 mm$^2$, 60 to 106 mm$^2$, 70 to 106 mm$^2$, 80 to 106 mm$^2$, 90 to 106 mm$^2$, 100 to 106 mm$^2$, 101 to 106 mm$^2$, 102 to 106 mm$^2$, 103 to 106 mm$^2$, 104 to 106 mm$^2$, 105 to 106 mm$^2$, 1 to 105 mm$^2$, 10 to 105 mm$^2$, 20 to 105 mm$^2$, 30 to 105 mm$^2$, 40 to 105 mm$^2$, 50 to 105 mm$^2$, 60 to 105 mm$^2$, 70 to 105 mm$^2$, 80 to 105 mm$^2$, 90 to 105 mm$^2$, 100 to 105 mm$^2$, 101 to 105 mm$^2$, 102 to 105 mm$^2$, 103 to 105 mm$^2$, 104 to 105 mm$^2$, 1 to 104 mm$^2$, 10 to 104 mm$^2$, 20 to 104 mm$^2$, 30 to 104 mm$^2$, 40 to 104 mm$^2$, 50 to 104 mm$^2$, 60 to 104 mm$^2$, 70 to 104 mm$^2$, 80 to 104 mm$^2$, 90 to 104 mm$^2$, 100 to 104 mm$^2$, 101 to 104 mm$^2$, 102 to 104 mm$^2$, 103 to 104 mm$^2$, or, 100 to 104 mm$^2$, 1 to 103 mm$^2$, 10 to 103 mm$^2$, 20 to 103 mm$^2$, 30 to 103 mm$^2$, 40 to 103 mm$^2$, 50 to 103 mm$^2$, 60 to 103 mm$^2$, 70 to 103 mm$^2$, 80 to 103 mm$^2$, 90 to 103 mm$^2$, 100 to 103 mm$^2$, 101 to 103 mm$^2$, or 102 to 103 mm$^2$. Suitable lengths for a photosensitive cardiac rhythm modulation tissue structure are about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 cm. Pediatric patients may require smaller photosensitive cardiac rhythm modulation tissue structures than adult patients. Values and ranges intermediate to the above-recited values and ranges are also contemplated by the present invention.

The shape of the photosensitive cardiac rhythm modulation tissue structure can be designed according to the needs of the patient. The overall shape of the photosensitive cardiac rhythm modulation tissue structure is optimized to possess desirable biological properties, and to efficiently deliver depolarizing current to the host myocardium with as few cells as possible. For example, an elliptical photosensitive cardiac rhythm modulation tissue structure mimics the shape of a normal human SA node. The shape of the photosensitive cardiac rhythm modulation tissue structure can also be designed to deliver a directional, polarizing current to the surrounding cardiac tissue. Suitable shapes for delivering a directional, polarizing current including, but are not limited to, triangles, ovals or teardrop shapes. A triangle shape allows tuning of the direction of the wavefront propagation.

Any suitable means for accessing the subject's heart and attaching the photosensitive cardiac rhythm modulation tissue structure and/or system may be used, such as thoracic surgery or transmyocardial catheter delivery. The photosensitive cardiac rhythm modulation tissue structure may be rolled up inside a transmyocardial catheter and unrolled at the site of attachment. The photosensitive cardiac rhythm modulation tissue structure may be attached in the epicardium or endocardium depending on the specific pacing need of the heart and the underlying cardiac disorder. Cardiomyoctes on the photosensitive cardiac rhythm modulation tissue structure form conductive gap junctions with the heart within 30-45 minutes of contact (Y. Haraguchi, et al., *Biomaterials* 27: 4765-4774, 2006). Thus, although no special securing mechanism or suturing is required to attach the photosensitive cardiac rhythm modulation tissue structure to the heart, a means is needed to hold the photosensitive cardiac rhythm modulation tissue structure in place on the heart until conductive junctions develop. These may include sutures or surgical adhesives.

IV. In Vitro Uses of Photosensitive Cardiac Rhythm Modulation Tissue Structures

The photosensitive cardiac cells and photosensitive cardiac rhythm modulation tissue structures described above can be used experimentally in vitro, for example, for tissue engineering, soft robotics, development of diagnostic methods, and drug discovery. Photosensitive cardiac rhythm modulation tissue structures can be studied alone or in combination with other photosensitive cardiac rhythm modulation tissue structures or other cells and tissues in culture. Photosensitive cells allow easy target selection with micron resolution. A single laser provides programmable multipoint stimulation of tissue with millisecond temporal resolution. Photo-activated cells can be combined with calcium and voltage-sensitive dyes to create an "all-optical" in vitro experimental model for electrophysiology as described in, for example, U.S. Provisional Application No. 61/174,511 and WO 2010/127280, the entire contents of which are incorporated herein by reference.

The present invention is next described by means of the following examples. However, the use of these and other examples anywhere in the specification is illustrative only, and in no way limits the scope and meaning of the invention or of any exemplified form. The invention is not limited to any particular preferred embodiments described herein. Many modifications and variations of the invention may be apparent to those skilled in the art and can be made without departing from its spirit and scope. The contents of all references, patents and published patent applications cited throughout this application, including figures, are incorporated herein by reference.

EXAMPLES

The following Materials and Methods were used in the Examples described below.

Materials and Methods

Myocyte Harvest and Culture

Cardiac myocytes are dissociated from ventricles of 2 day old neonatal Sprague-Dawley rats using trypsin and collagenase and resuspended in M199 culture medium supplemented with 10% heat-inactivated FBS, 10 mM HEPES, 3.5 g/L glucose, 2 mM L-glutamine, 2 mg/L vitamin B-12, and 50 U/mL penicillin. Isolated cells are differentially preplated in two 45 minute steps and re-suspended in culture medium. The standard bathing solution for electrophysiological studies contains 137 mM NaCl, 5.4 mM KCl, 1.2 mM $MgCl_2$, 1 mM $CaCl_2$, 20 mM HEPES (pH=7.4, warmed to 36° C. for experiments). For calcium ion imaging, micropatterned myocytes are exposed to 5 μM fluo-3 AM (diluted from stock solutions containing 50 μg fluo-3 AM, 25 μg Pluronic (Molecular Probes, Eugene, Oreg.) in 100 μL dimethyl sulfoxide) for 5 minutes followed by a 30 minutes wash in extracellular solution to allow time for deesterification.

Pacemaker cells are harvested in a similar fashion. Atrial myocytes are isolated from 2 day-old Sprague Dawley rats as described above. Excised right atrial tissue is agitated in a 0.1% trypsin solution cooled to 4° C. for approximately 14 hours. Trypsinized atria are dissociated into their cellular constituents via serial exposure to a 0.1% solution of collagenase type II at 37° C. for 2 minutes. The myocyte portion of the cell population is enriched by passing the dissociated cell solution through a nylon mesh with 40 μm pores, and then pre-plating twice for 45 minutes each time. Isolated myocytes are seeded onto muscular thin film substrates with patterned fibronectin matrices and grown in culture medium consisting of Medium 199 base supplemented with 10% heat-inactivated fetal bovine serum, 10 mM HEPES, 20 mM glucose, 2 mM L-glutamine, 1.5 μM vitamin B-12, and 50 U/ml penicillin. On the second day of culture, the serum concentration of the medium is reduced to 2%, and the medium is changed every 48 hours thereafter.

MTF Fabrication

PDMS thin film substrates are fabricated via a multi-step spin-coating process. Glass cover slips (25 mm diameter) are cleaned by sonicating for 60 minutes in 95% ethanol and air dried. Next, poly(N-isopropylacrylamide) (PIPAAM, Polysciences) is dissolved at 10 wt % in 99.4% 1-butanol (w/v) and spin-coated onto the glass cover slips for 1 minute at 6,000 RPM. Sylgard 184 (Dow Corning) polydimethylsiloxane (PDMS) elastomer is mixed at a 10:1 base to curing agent ratio and spin-coated on top of the PIPAAM coated glass cover slip. Once mixed, the PDMS prepolymer slowly increases in viscosity reaching gelation at ~8 hours. Thicker PDMS layers are formed by spin-coating higher viscosity PDMS prepolymer between 0 and 6 hours post mixing allowing films from 14 to 60 μm thick to be formed. PDMS coated cover slips are then cured either at room temperature (~22° C.) for 48 hours or at 65° C. for 4 hours. Different curing temperatures are used to control the curvature of the PDMS film when it is released from the cover slip upon dissolution of the PIPAAM layer.

PDMS Surface Functionalization

The PDMS thin films are coated with either an isotropic or patterned layer of fibronectin (FN, Sigma). In either case, immediately prior to FN treatment the PDMS-coated cover slips are oxidized using UV ozone (Model No. 342, Jetlight Company, Inc.) for 8 minutes to sterilize the surface and increase hydrophilicity for microcontact printing (μCP) (Tan et al., Tissue Eng 10: 865-72, 2004). Subsequent processing is performed in a biohood under sterile conditions. Isotropic FN is deposited by placing a 1 mL droplet of 25 μg/mL FN in sterile deionized (DI) water on the PDMS and incubating for 15 minutes. It is essential that water does not contact the periphery of the cover slip during this or any subsequent step because it would seep under the PDMS and prematurely dissolve the PIPAAM. Following FN incubation, excess protein is removed by washing three times with DI water and then air drying prior to cardiomyocyte seeding.

Anisotropic patterning of FN is performed using μCP. The basic μCP technique is well established and allows the rapid patterning of biomolecules on a variety of planar substrates using PDMS stamps. PDMS stamps are used to pattern alternating high and low density lines of FN on the PDMS coated glass cover slips in order to form anisotropic two-dimensional myocardium, as based on previously published methods. PDMS stamps are fabricated with 20 μm wide, 2 μm tall ridges separated by 20 μm spacing. Briefly, silicon wafers are spin-coated with SU-8 photoresist (Microchem) and exposed to UV light through a photomask selectively cross-linking regions of the photoresist. The photoresist is then developed and the non-exposed regions are removed. A negative of the patterned photoresist wafer is formed by casting PDMS prepolymer against it. Prior to each use, the PDMS stamps are sonicated in 50% ethanol for 30 minutes to sterilize and remove surface contaminants. Once dried, the PDMS stamp is inked with a 250 μL droplet of 50 μg/mL FN in DI water and incubated for 1 hour. The stamp is then rinsed twice in DI water to remove excess protein and dried under a stream of compressed air. High density FN lines are transferred from the stamp to the PDMS thin film by making conformal contact for 1 minute. Upon stamp removal a background surface chemistry is applied to the region in between the high density FN lines. To prevent cell adhesion in between the lines and create an array of discrete muscle fibers, a droplet of 1% Pluronics F127 (BASF Group) in DI water is spread over the patterned area and incubated on the PDMS surface for 15 minutes. To create anisotropic two-dimensional myocardium, low density FN lines in between the high density FN lines are used. A droplet of 2.5 μg/mL FN in DI water is spread over the patterned area and incubated on the PDMS surface for 15 minutes. Following the incubation period, the PDMS film is washed three times with DI water, air dried and then seeded with pacemaking cells according to the protocol above.

Immunostaining

Gap junctions and adherens junctions are detected by immunofluorescence as follows: Samples are first permeabilized in a cytoskeletal stabilizing buffer (300 mM sucrose, 100 mM NaCl, 3 mM $MgCl_2$, 0.5% TritonX100, 10 mM Pipes, pH 6), then fixed in 4% paraformaldehyde for 15 minutes and washed with PBS. To prevent nonspecific binding of secondary antibodies, a blocking procedure is used that includes incubation for 15 minutes in 5% serum from the species source of the secondary antibody, 1% BSA in PBS. The samples are then incubated with primary antibody to the desired target in PBS for 1 hour, washed, incubated in fluorescently-labeled secondary antibody in PBS for 1 hour, and washed.

For histological examination, implanted pacemaker constructs are placed in tissue embedding medium (Histo-Prep™, Fisher Scientific) and frozen at −80° C. Frozen samples are cryosectioned, mounted on Superfrost Plus glass slides (Fisher Scientific), and stored at −80° C. Immunohistochemical analysis of samples is conducted by immersing constructs in a solution of 4% paraformaldehyde and 0.5 μL/mL Triton X-100 for 15 minutes. Mouse monoclonal antibodies raised against connexin 40 and connexin 43 are used to label connexin channels between ventricular myocytes and atrial pacemaker cells. Labeled proteins are visualized by applying goat anti-mouse IgG secondary antibodies conjugated to either Alexa Fluor 488 or Alexa Fluor 594.

Transfection of Green Fluorescent Protein (GFP) Plasmids

Transfection of atrial myocytes with gfp expression plasmids are accomplished with a component system formed by preincubation of Ad5d1312 adenovirus and poly-L-lysine. The expression plasmid is used to transfect cells that are cultured on micropatterned islands as described above. Fluorescent microscopy is used to verify transfection efficiency. Transient transfection of gfp- and yfps, such as gfp-paxillin, is accomplished using Effectene transfection reagent (Qiagen, Chatsworth, Calif.).

Optical Mapping of 2-D Engineered Cardiac Cells

The optical mapping system (OMS) is a high-speed, high-sensitivity 124-channel photodiode system that is optimized for dynamic fluorescence imaging of voltage-sensitive and calcium-sensitive dyes (see, FIG. 3). The OMS consists of 124 independent optical fibers arranged in a honeycomb array, connected through the baseport of an inverted microscope. Each fiber is connected to a discrete photodiode transimpedance amplifier. The current through each photodiode is amplified by a 100 MSΩ/A transimpedance gain, AC-coupled, and scaled by a non-inverting gain of 10 V/V prior to discretization by a 12-bit A/D converter. Signal bandwidth is hardware-limited to 2.5 kHz to minimize front-end noise while providing adequate bandwidth to detect action potentials. Maximum spatial resolution is 10 μm. Maximum sample rate is 5 kHz (200 μs) when all pixels are recorded, and can be increased up to 200 kHz (50 μs) when a subset of pixels is recorded. Fluorescence signals from each optical fiber are low-pass filtered at 100 Hz, normalized, and $dV_m/dt$ is calculated by a 5-point numerical derivative. Activation times are determined by $dV_m/dt_{max}$. Conduction velocity vector fields are calculated from activation maps, shown in FIG. 4.

Optical recordings of transmembrane potential ($V_m$) are performed in Tyrode's solution of the following composition (in mM): NaCl 135.0, $CaCl_2$ 1.8, KCl 5.4, $MgCl_2$ 1.0, $NaH_2PO_4$ 0.33, HEPES 5.0 and glucose 5.0. The excitation-contraction uncoupler, Blebbistatin (10 μM, Calbiochem), is added to the solution to reduce motion artifacts. The pH is adjusted to 7.4 and the temperature maintained at 35° C.

Fluorescence recordings are obtained with the voltage sensitive dye RH237 (Invitrogen). A 2 mM stock solution of RH237 in dimethyl sulfoxide (Sigma) is prepared and stored at 4° C. The stock solution is diluted in Tyrode's solution to a final concentration of 8 μM. Cell cultures are incubated in the dye solution for 5 minutes, washed 3 times with Tyrode's solution, and incubated in Tyrode's solution containing Blebbistatin for 10 minutes before imaging. Using an inverted microscope (Zeiss Axiovert 200) with a 40× objective (Zeiss EC Plan-NEOFLUAR, numerical aperture 1.3), fluorescence recordings are obtained. Cell cultures are exposed for 1-2 sec to excitation light (530-585 nm). Emitted light is longpass filtered at 615 nm and focused onto the hexagonal array of 124 optical fibers each coupled to a photodiode. At 40×, each optical fiber corresponds to a 25 μm-diameter tissue area. The photocurrent from each diode is converted to a voltage, amplified and digitized at 12-bit resolution at a sampling rate of 5 kHz.

Optical Mapping of Isolated Rat Hearts

After intraperitoneal (IP) injection of 300 units heparin, rats are anesthetized with sodium pentobarbital (50 mg/kg IP). Once surgical-depth anesthesia is reached, hearts are quickly excised via a midsternal incision. Hearts are placed on a Langendorff apparatus and retrogradely perfused through the aorta with warm (36° C.), oxygenated (95% $O_2$, 5% $CO_2$) modified Tyrode's solution of the following composition (in mM): NaCl 128.2, $CaCl_2$ 1.3, KCl 4.7, $MgCl_2$ 1.05, $NaH_2PO_4$ 1.19, $NaHCO_3$ 20 and glucose 11.1 (FIG. 5). The pH is maintained at 7.4 by adjusting the $CO_2$. The perfusion rate is adjusted to maintain an aortic pressure of 60-70 mmHg. The excitation-contraction uncoupler, Blebbistatin (10 μM, Calbiochem, La Jolla, Calif.), is added to the perfusate to eliminate motion artifacts in the optical recordings caused by muscle contraction. The heart is then stained with the voltage-sensitive dye di-4-ANEPPS (5 minutes, 1.3 μM in the perfusate). Optical action potentials are recorded at high spatial resolution using a MiCAM Ultima-L CMOS camera (0.1 ms, 100×100 pixels). Optical fluorescence signals (F) are recorded from a region of approximately 30×30 mm with a spatial resolution of 300 μm at a rate of 1000-5000 frames/s. The signals are low-pass filtered, differentiated (dF/dt), normalized, plotted as two-dimensional intensity graphs, and overlapped as frames with the image of the preparation to produce animations.

Example 1

Construction of Pacing Muscular Thin Films

Tissue engineered pacemakers are made by harvesting the sinoatrial node from neonatal rat right atria, chemically dissociating the cells, and culturing them on micropatterned MTFs. More specifically, the right atria from neonate rats is harvested, carefully dissected, and those myocytes in the region of the sinoatrial node are chemically dissociated. These myocytes are cultured on micropatterned MTFs to form an anisotropic tissue structure with autonomous beating capability.

To demonstrate that the tissue engineered pacemaker is capable of integration into and pacing control of cardiac tissue in vitro, immunohistochemical analysis is performed of a pacing MTF placed on and attached to engineered ventricular myocardium (FIG. 5). Staining is used to demonstrate the formation of gap junctions between the ventricular myocardium and the pacemaking cells. It has been shown that ventricular myocytes predominantly express C×43 gap junctions and that atrial myocytes primarily express C×40 gap junctions and that these proteins will form a conductive heterotypic gap junction that will support propagation of an action potential between two myocytes. Therefore, after staining for both of these proteins, confocal microscopy is used to demonstrate that the GFP-expressing atrial myocytes are electrically coupling to the ventricular myocytes of the larger engineered tissue. Furthermore, immunostaining for cadherins is also used to show the formation of junctions between the atrial and ventricular myocytes.

Furthermore, to demonstrate functional coupling of the pacemaker to the tissue, physiological experiments with the optical mapping system described above are conducted to spatially map action potential propagation. Pacing control of the engineered myocardium with the pacing MTF is further demonstrated by using channel blockers against leaky $Na^+$ ion channels which drive the autonomous pacing capability of the pacemaking cells. The efficacy of the pacemaker is shown by wash in-wash out of the channel blockers in conjunction with optical mapping.

Example 2

Surgical Implantation of Pacing Muscular Thin Films in Rats

Surgical implantation of pacing MTFs is accomplished by surgically ablating the sinoatrial node in anaesthetized rats and sewing pacing MTFs on the apical surface of the right atria. More specifically, surgical ablation of the sinoatrial node is accomplished by cauterizing the node in vivo during survival surgery (Tarnayski et al., *Physiol. Genomics:* 16: pp. 349-360, 2004). Pacing is restored by implantation of a pacing MTF constructed as described in Example 1. Briefly, 70 mg/kg of pentobarbital sodium is administered to induce anesthesia. After an adequate depth of anesthesia is attained, the rat is placed in a supine position and a taut 5-0 ligature is situated behind the front upper incisors to keep the neck slightly extended. The tongue is retracted and held with forceps while inserting a 20 gauge catheter into the trachea. The catheter is then attached to a ventilator via a Y-shaped connector. Ventilation is performed using a tidal volume of 200 uL and a respiratory rate of 133/min with 100% oxygen provided to the inflow of the ventilator. Prior to incision, the chest is disinfected with betadine solution, 70% ethyl alcohol, and 0.1 mL of 0.1% lidocaine introduced under the skin. The chest cavity is opened by an incision 1 to 2 mm above the left armpit and a chest retractor is applied to allow visualization of the heart. The pericardial sac is opened and pulled apart, the right atria is identified and its apical surface burned with a cauterizing electrode. When atrial contractions cease, a previously prepared pacing MTF is sewn onto the atrial surface with a 7-0 silk suture. Finally, the lungs are over-inflated, and the chest cavity, muscles and skin are closed layer by layer with 6-0 nylon and 6-0 absorbable (for muscles) sutures. The duration of the entire procedure is approximately 15-20 min.

Hearts of surviving rats are harvested for optical mapping studies. If the pacing MTF is successfully implanted, the heart will have a unique activation sequence with the earliest activation arising from the location of the pacemaking MTF. This activation sequence will not be replicated in control experiments accomplished by pacing the heart at other locations. Furthermore, the right atria with the pacing MTF attached is harvested for in vitro optical mapping experiments and postmortem histology. Immunostaining is performed to demonstrate the formation of gap junctions from Cx 40, 43, and 45, the formation of adherens junctions, as well as to mark localized angiogenesis, fibrosis, and neural innervation. Additionally, myocytes on the pacing MTF are transfected with gfp prior to implantation and fluorescent microscopic examination of the right atria post mortem is used to determine if any of these cells migrated away from the graft site.

Example 3

Generation of Photoinduced Action Potentials in 2-Dimensional Genetically Engineered Photosensitive Cardiac Tissue Isotropic and anisotropic 2-dimensional genetically engineered photosensitive cardiac tissues are prepared as described herein. In general, one or more of the cells used to prepare the 2-dimensional genetically engineered photosensitive cardiac tissue is genetically modified to express a photosensitive membrane transport mechanism for the purpose of generating photoinduced action potentials. Genetic modification is carried out via viral or non-viral transfection. Alternatively, tissues fabricated from cells derived from a cell line which stably expresses a photosensitive membrane transport mechanism may be used to prepare isotropic and anisotropic 2-dimensional genetically engineered photosensitive cardiac tissues. Suitable cells for preparation of these tissues include, but are not limited to, primary mammalian cardiac myocytes, cardiac cells derived from embryonic stem cells, induced pluripotent stem (iPS) cells, adult mesenchymal stem cells, adult cardiac resident stem cells, and other adult stem cells (e.g., hematopoietic cells, fat cells).

In order to demonstrate that the 2-dimensional genetically engineered photosensitive cardiac tissue is responsive to optical activation, the tissue is stained with a voltage sensitive dye and optically mapped as described supra. A location on the tissue offset from the observation site is photostimulated by a light source comprised of a high intensity light-emitting diodes (LED), a diode laser, or other light source coupled to an optical fiber. Propagation of action potentials emanating from the photostimulation site at a consistent frequency, higher than the native escape frequency of the cells comprising the genetically engineered photosensitive tissue, demonstrates the photoexcitability of the tissue. Further evidence is provided by the photoinduced propagation of Ca2+ waves, as imaged by a Ca2+ sensitive dye.

As an alternative to optical mapping, the electrophysiology of a cell within the sample is observed by the patch clamp method. A cell expressing the photosensitive membrane transport mechanism is held in a current or voltage clamp. Upon photostimulation, a photoinduced action potential or current, respectively, is detected.

Example 4

Optical Pacing of a Photosensitive Cardiac Rhythm Modulation Tissue Structure

A photosensitive cardiac rhythm modulation tissue structure is prepared as described herein for the purpose of generating photoinduced action potentials.

To demonstrate the optical pacing of the photosensitive cardiac rhythm modulation tissue structure, the tissue structure is sectioned allowing for the free release and contraction of an individual tissue structure section. An individual tissue structure section is mounted in an assay device and a light source is focused onto a portion of the section. Pulse frequency and intensity of the light source is adjusted until the beating of the section is "captured", i.e. the tissue structure section is contracting in synchronization with the light source pulse.

I claim:
1. A photosensitive rhythm modulation tissue structure, comprising
   a flexible polymer layer and
   a genetically engineered anisotropic photosensitive tissue attached to the flexible polymer layer and comprising a population of electrically coupled pacing cells expressing a photosensitive membrane transport mechanism, the photosensitive rhythm modulation tissue structure in contact with a voltage-sensitive or a calcium-sensi- tive dye enabling optical detection of an electrophysiological change in the electrically coupled pacing cells.

2. A photosensitive rhythm modulation system comprising
the photosensitive rhythm modulation tissue structure of claim 1; and
a light source adapted to provide photostimulation to the photosensitive rhythm modulation tissue structure.

3. A photosensitive pacemaker comprising the photosensitive rhythm modulation system of claim 2, wherein the genetically engineered photosensitive tissue is capable of depolarizing, generating an action potential, and beating in response to photostimulation.

4. A photosensitive defibrillator comprising the photosensitive rhythm modulation system of claim 2, wherein the genetically engineered photosensitive tissue is capable of hyperpolarizing, suppressing generation of an action potential, and suppressing beating in response to photostimulation.

5. An in vitro model for electrophysiological studies of tissue function comprising a plurality of the photosensitive rhythm modulation tissue structures of claim 1.

6. A method for identifying a compound that modulates a tissue activity, the method comprising the steps of
a) providing the in vitro model of claim 5;
b) contacting the model with a test compound; and
c) evaluating the activity of the model in response to the test compound, thereby identifying a compound that modulates a tissue activity.

7. The photosensitive rhythm modulation tissue structure of claim 1, wherein the flexible polymer layer comprises at least one of:
a thermoplastic polymer;
a thermosetting polymer;
a non-degradable polymer; and
a non-elastomer, biodegradable polymer.

8. The photosensitive rhythm modulation tissue structure of claim 7, wherein the flexible polymer layer comprises polydimethylsiloxane.

9. The photosensitive rhythm modulation tissue structure of claim 1, wherein the flexible polymer layer and the genetically engineered photosensitive tissue define a specific shape, the specific shape being one of a triangle, an oval, and a teardrop.

10. The photosensitive rhythm modulation tissue structure of claim 9, wherein the specific shape is a triangle.

11. The photosensitive rhythm modulation tissue structure of claim 1, wherein the flexible polymer layer comprises a biopolymer.

12. The photosensitive rhythm modulation tissue structure of claim 1, wherein the flexible polymer layer comprises a hydrogel.

13. The photosensitive rhythm modulation tissue structure of claim 1, wherein the flexible polymer layer comprises polylactic acid.

14. The photosensitive rhythm modulation tissue structure of claim 1, wherein the flexible polymer layer comprises polyglycolic acid.

15. The photosensitive rhythm modulation tissue structure of claim 1, wherein the pacing cells are muscle cells.

16. The photosensitive rhythm modulation tissue structure of claim 15, wherein the muscle cells are cardiac myocytes.

17. The photosensitive rhythm modulation tissue structure of claim 15, wherein the muscle cells are atrial myocytes.

18. The photosensitive rhythm modulation tissue structure of claim 1, wherein the pacing cells adhere to the flexible polymer layer in an anisotropic arrangement.

19. The photosensitive rhythm modulation system of claim 2, further comprising a sensor array.

20. The photosensitive rhythm modulation tissue structure of claim 1, wherein the pacing cells are cardiac cells.

21. The photosensitive rhythm modulation tissue structure of claim 1, wherein the photosensitive membrane transport mechanism includes a light-gated ion channel.

22. The photosensitive rhythm modulation tissue structure of claim 1, wherein the photosensitive membrane transport mechanism includes a light-driven ion pump.

23. The photosensitive rhythm modulation tissue structure of claim 1, wherein the photosensitive membrane transport mechanism comprises a rhodopsin.

* * * * *